United States Patent [19]
Yoon

[11] Patent Number: 5,814,026
[45] Date of Patent: Sep. 29, 1998

[54] ENDOSCOPIC PORTAL HAVING A UNIVERSAL SEAL AND METHODS FOR INTRODUCING INSTRUMENTS THERETHROUGH

[76] Inventor: InBae Yoon, 2101 Highland Ridge Dr., Phoenix, Md. 21131

[21] Appl. No.: 618,328

[22] Filed: Mar. 19, 1996

[51] Int. Cl.[6] .................................................. A61M 25/00
[52] U.S. Cl. .......................................................... 604/280
[58] Field of Search ................................... 604/167, 256, 604/249, 280, 264

[56] References Cited

U.S. PATENT DOCUMENTS

| | | |
|---|---|---|
| 1,986,484 | 11/1935 | Schlueter . |
| 3,565,078 | 2/1971 | Vaillialncourt . |
| 3,585,996 | 6/1971 | Reynolds . |
| 3,620,500 | 11/1971 | Santomieri . |
| 3,994,287 | 11/1976 | Turp et al. . |
| 4,177,814 | 12/1979 | Knepshield et al. . |
| 4,180,068 | 12/1979 | Jacobsen et al. . |
| 4,240,411 | 12/1980 | Hosono . |
| 4,243,034 | 1/1981 | Brandt . |
| 4,475,548 | 10/1984 | Muto . |
| 4,535,773 | 8/1985 | Yoon . |
| 4,654,030 | 3/1987 | Moll et al. . |
| 4,842,591 | 6/1989 | Luther . |
| 4,874,378 | 10/1989 | Hillstead . |
| 4,899,729 | 2/1990 | Gill et al. . |
| 4,917,668 | 4/1990 | Haindl ..................................... 604/167 |
| 4,929,235 | 5/1990 | Merry et al. . |
| 4,978,341 | 12/1990 | Niederhauser . |
| 4,994,027 | 2/1991 | Farrell . |
| 5,104,389 | 4/1992 | Deem et al. . |
| 5,108,380 | 4/1992 | Herlitze et al. . |
| 5,127,626 | 7/1992 | Hilal et al. . |
| 5,141,498 | 8/1992 | Christian ................................ 604/167 |
| 5,156,596 | 10/1992 | Balbierz et al. ........................ 604/167 |
| 5,158,553 | 10/1992 | Berry et al. . |
| 5,161,773 | 11/1992 | Tower . |
| 5,167,636 | 12/1992 | Clement . |
| 5,176,659 | 1/1993 | Mancini . |
| 5,180,373 | 1/1993 | Green et al. . |
| 5,188,607 | 2/1993 | Wu ........................................... 604/167 |
| 5,195,980 | 3/1993 | Catlin ...................................... 604/167 |
| 5,197,955 | 3/1993 | Stephens et al. . |
| 5,201,714 | 4/1993 | Gentelia et al. . |
| 5,207,656 | 5/1993 | Kranys . |
| 5,269,763 | 12/1993 | Boehmer et al. . |
| 5,282,790 | 2/1994 | Clement . |
| 5,300,035 | 4/1994 | Clement . |
| 5,308,336 | 5/1994 | Hart et al. .............................. 604/167 |

(List continued on next page.)

*Primary Examiner*—Manuel Mendez

[57] ABSTRACT

An endoscopic portal for establishing communication with a body cavity for the introduction of instruments through the endoscopic portal includes a seal having a variable size passage for communication with the body cavity to permit instruments of varying sizes to be passed therethrough and a tubular expander aligned with the variable size passage. The seal is biased to a contracted position wherein the variable size passage has a first cross sectional size and is movable to an expanded position wherein the variable size passage has a second cross sectional size larger than the first cross sectional size. The tubular expander has a blunt end insertable in the variable size passage to move the seal from the contracted position to the expanded position such that an instrument having a cross sectional size larger than the first cross sectional size can be introduced through the expander and the seal into the body cavity without contacting the seal. Thereafter, the blunt end of the tubular expander is withdrawable from the variable size passage such that the seal engages the instrument in the variable size passage to form a seal therewith. A method of introducing an instrument in a body cavity according to the present invention comprises the steps of moving a blunt end of a tubular expander into a variable size seal to enlarge the variable size seal, introducing an instrument through the tubular expander into the body cavity such that a distal end of the instrument is moved through the seal without contacting the seal and withdrawing the blunt end of the tubular expander from the seal such that the seal sealingly engages the instrument.

28 Claims, 9 Drawing Sheets

U.S. PATENT DOCUMENTS

| | | |
|---|---|---|
| 5,324,270 | 6/1994 | Kayan et al. . |
| 5,350,364 | 9/1994 | Stephens et al. . |
| 5,360,417 | 11/1994 | Gravener et al. .................. 604/167 |
| 5,376,077 | 12/1994 | Gomringer ....................... 604/167 |
| 5,385,553 | 1/1995 | Hart et al. ........................ 604/167 |
| 5,389,080 | 2/1995 | Yoon ................................ 604/167 |
| 5,391,153 | 2/1995 | Haber et al. . |
| 5,441,486 | 8/1995 | Yoon . |
| 5,460,616 | 10/1995 | Weinstein ......................... 604/167 |
| 5,476,475 | 12/1995 | Gadberry . |
| 5,492,304 | 2/1996 | Smith et al. ....................... 604/167 |
| 5,496,280 | 3/1996 | Vandenbroek et al. . |

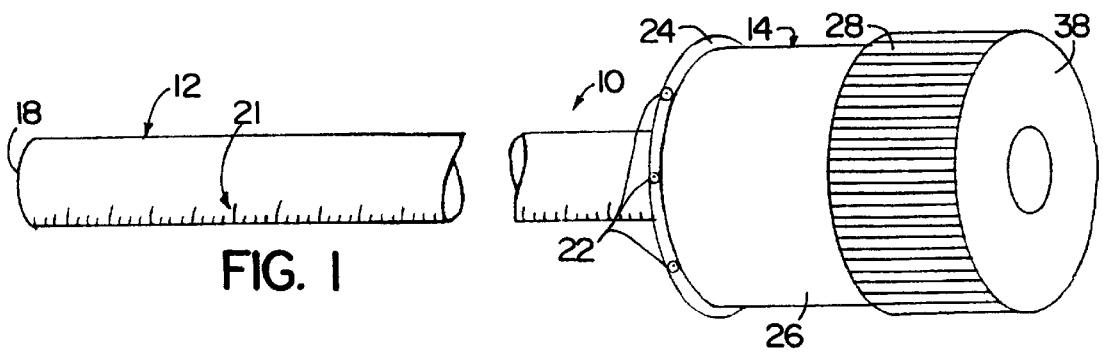
FIG. 1  FIG. 2
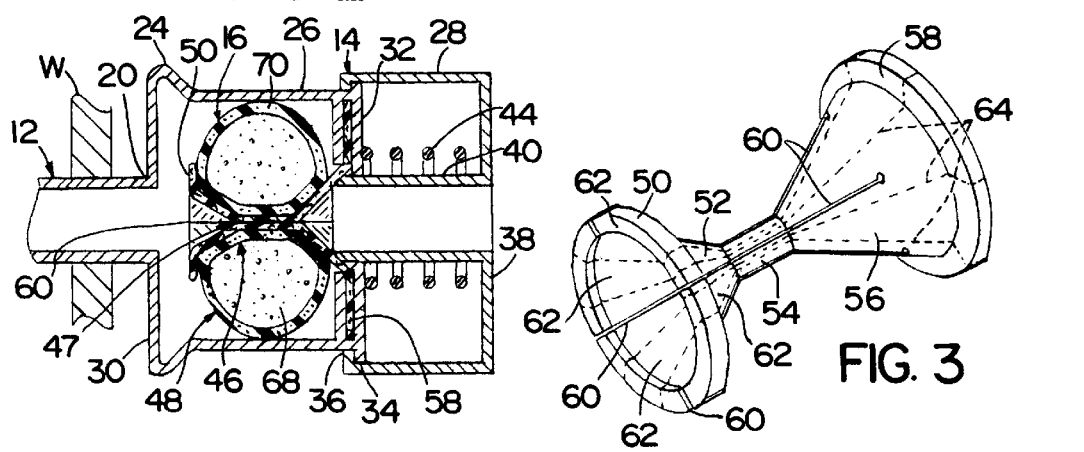
FIG. 3
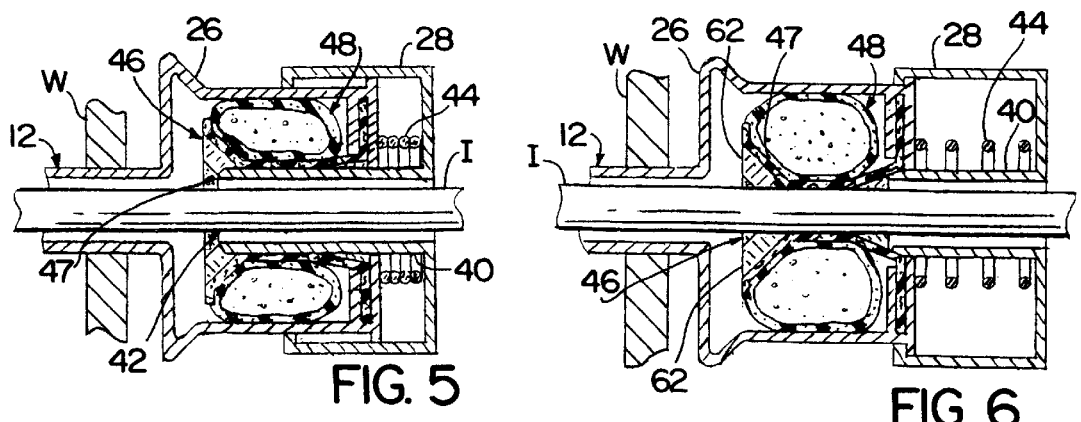
FIG. 5  FIG. 6
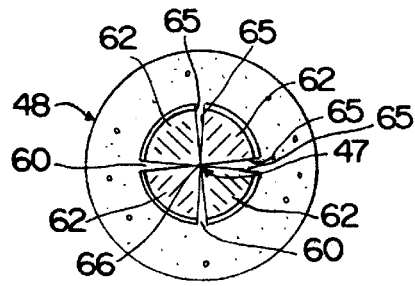 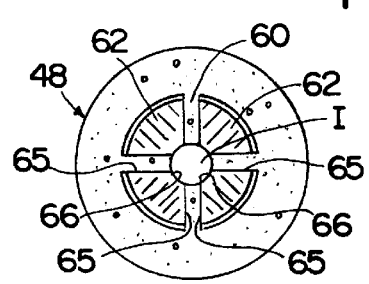
FIG. 4  FIG. 7

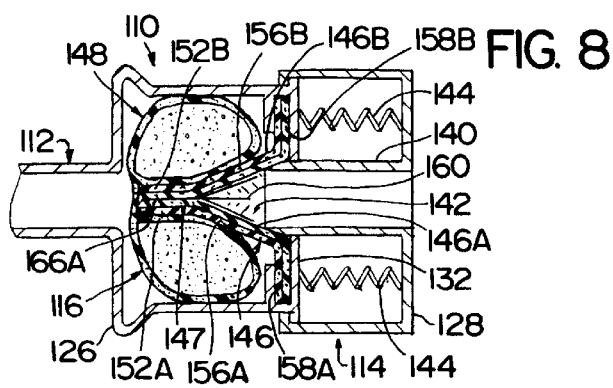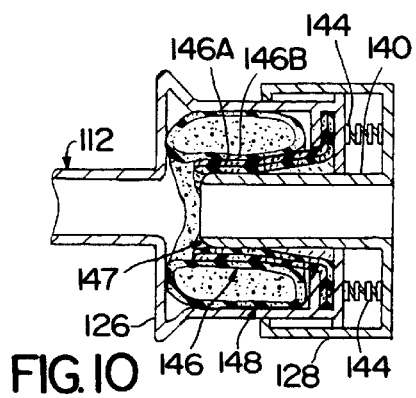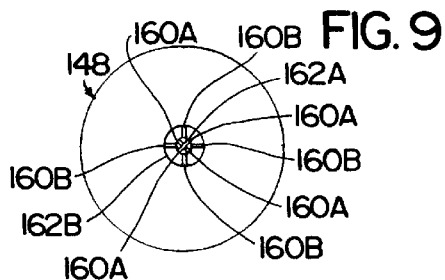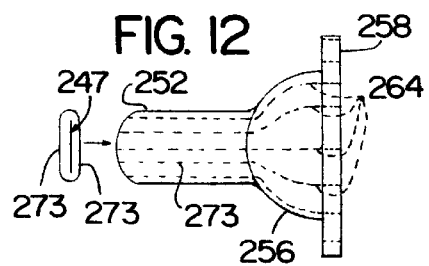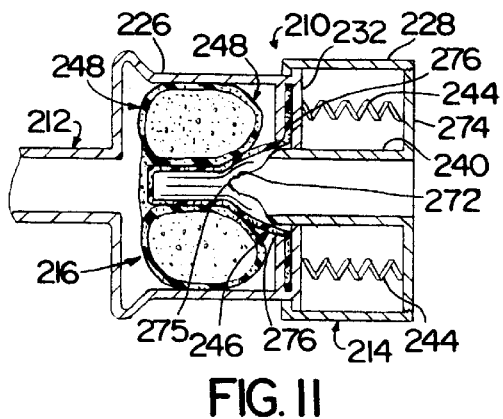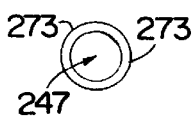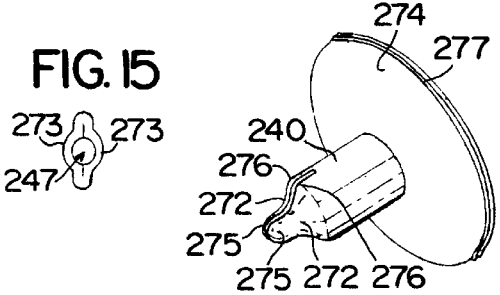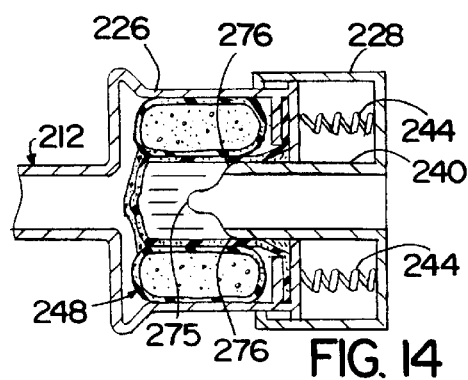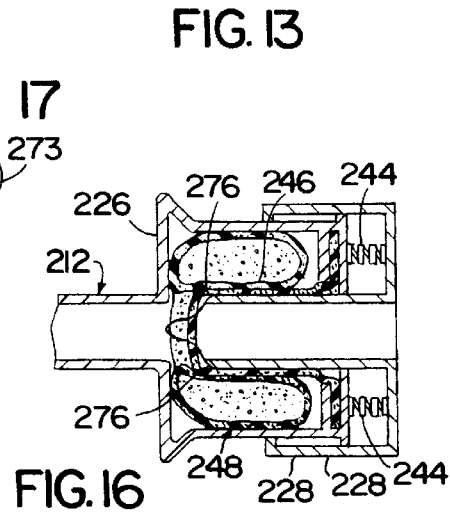

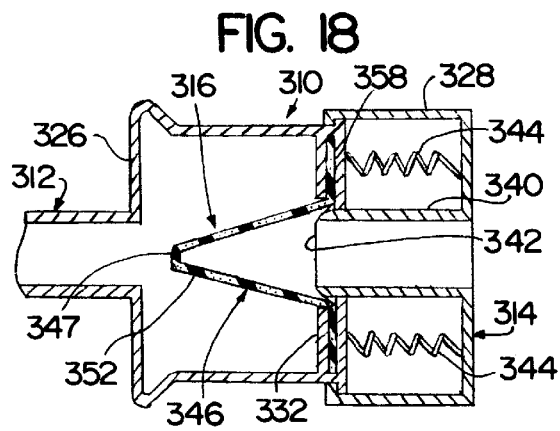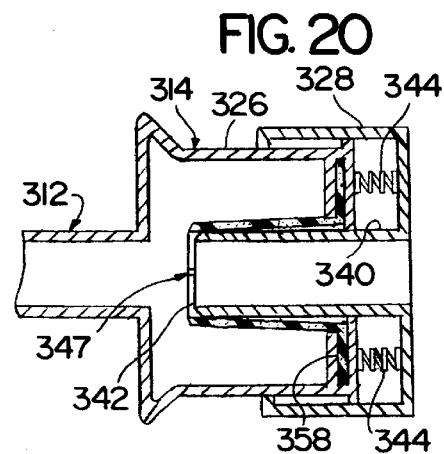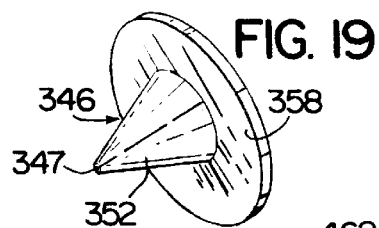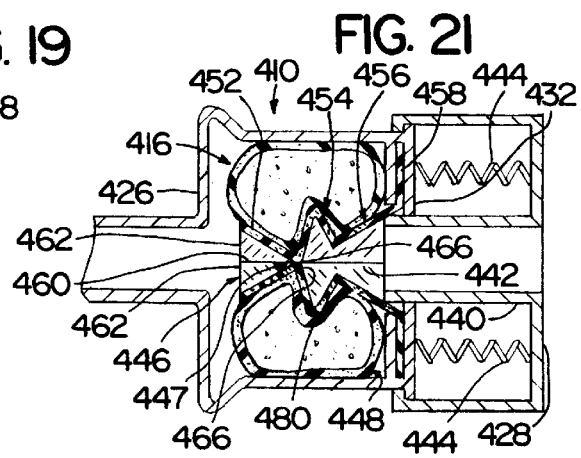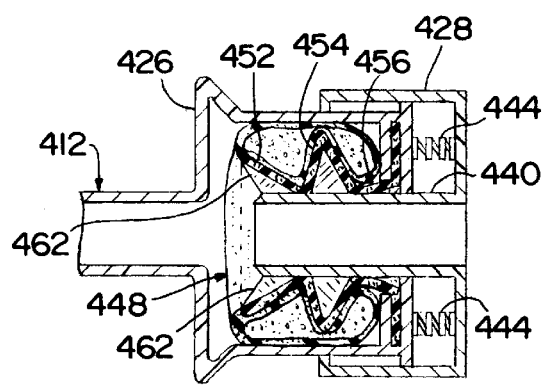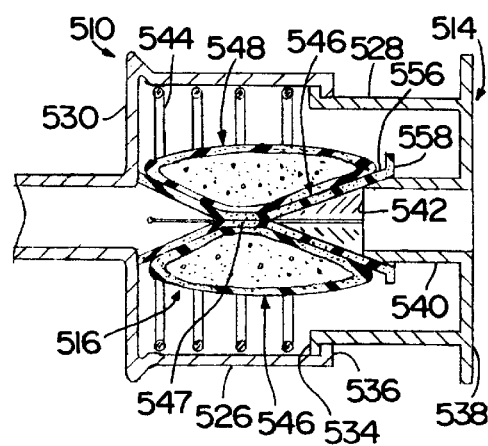

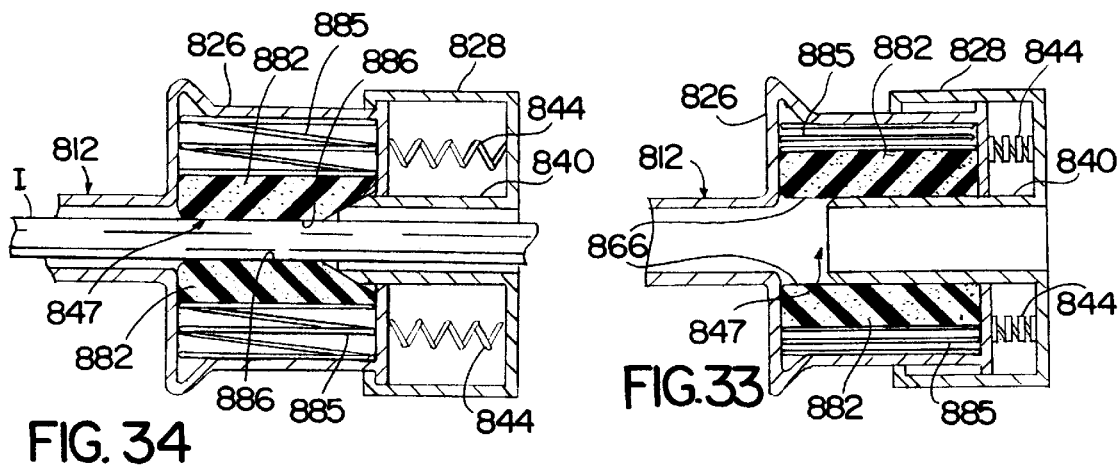
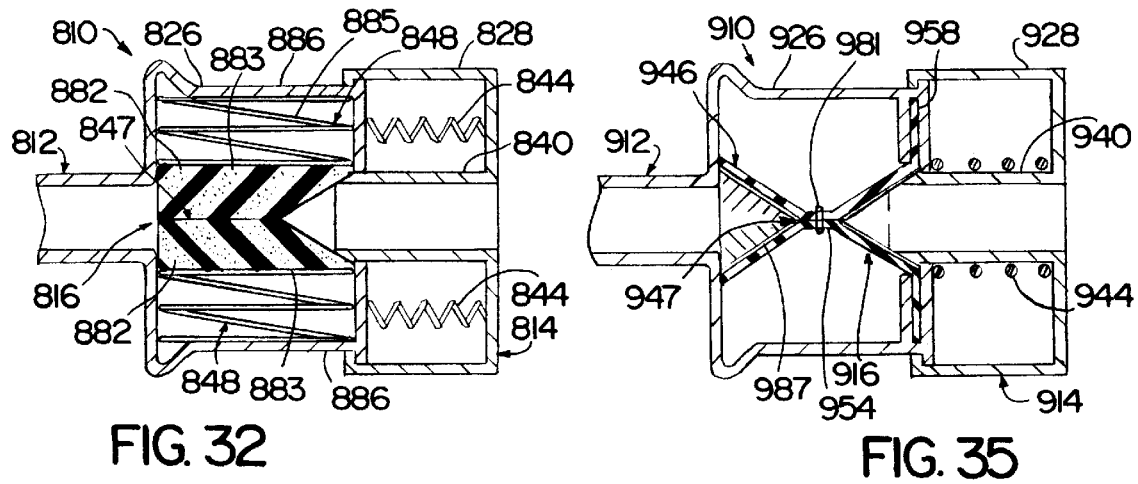
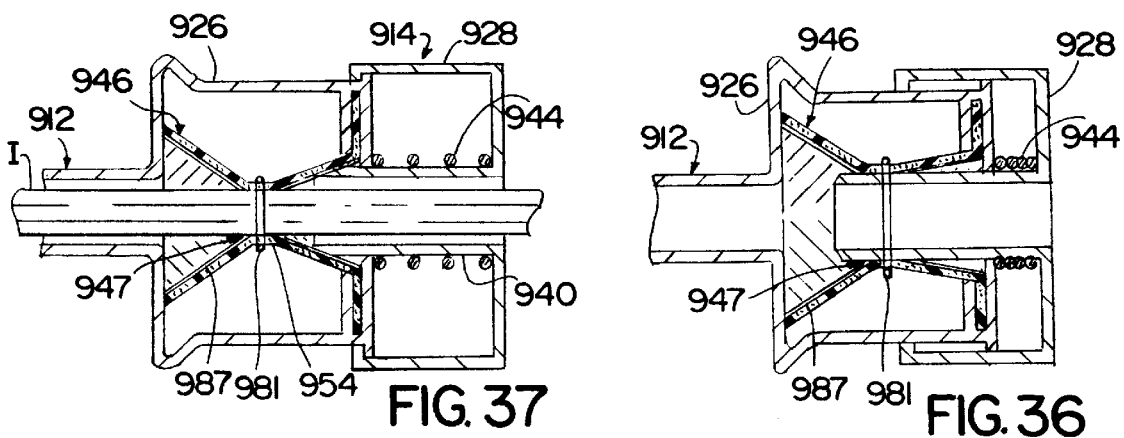
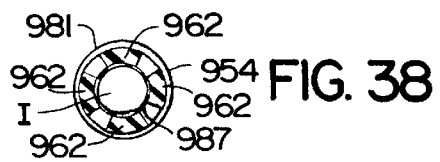

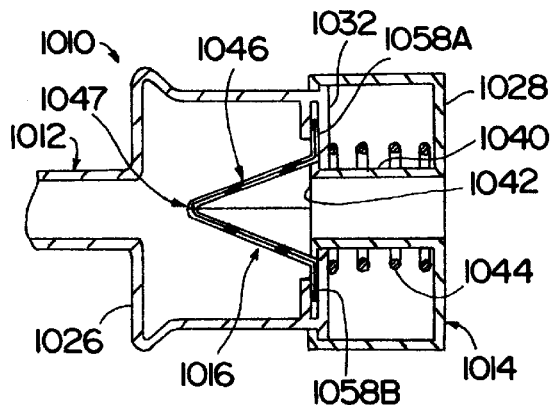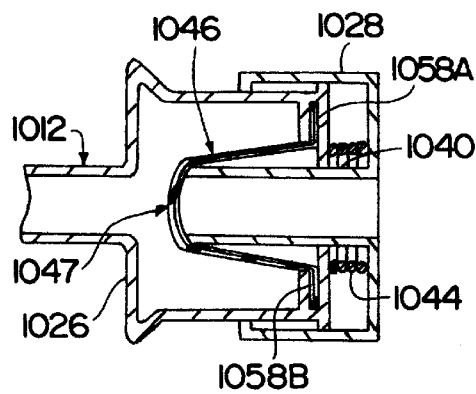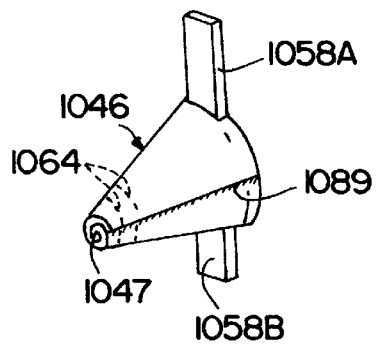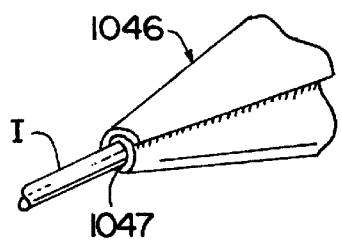

ENDOSCOPIC PORTAL HAVING A UNIVERSAL SEAL AND METHODS FOR INTRODUCING INSTRUMENTS THERETHROUGH

BACKGROUND OF THE INVENTION

1. Field of the Invention

The present invention pertains to endoscopic portals for establishing communication with an internal site in a body and, more particularly, to endoscopic portals having universal seals forming a seal with instruments of various sizes introduced through the endoscopic portals and to methods for introducing instruments through such universal seals.

2. Brief Description of the Prior Art

In endoscopic procedures, a portal, such as a sleeve or cannula or other structure forming a passage, is normally disposed in a cavity wall such that a distal end of the portal is positioned within the cavity and a proximal end of the portal is disposed externally of the cavity to provide a passage establishing communication with an internal site from externally of the cavity. Typically, various instruments are introduced at the operative site through the passage defined by the portal in order to perform diagnostic and/or surgical procedures, with the instruments many times having varying sizes in cross-section. In endoscopic procedures, it is important to prevent undesired fluid flow to and from the internal site; and, accordingly, the portal must be sealed prior to and subsequent to the introduction of instruments and while the instruments are in place. In particular, fluids such as gaseous phase carbon dioxide or nitrous oxide are normally introduced in the body for insufflation as part of the endoscopic procedure, and the escape of such gases through the portal should be prevented.

Many endoscopic portals have valves including a valve passage having a fixed size. Instruments larger in size than the fixed size of the valve passage cannot be inserted through the valve passage into the portal; and, when instruments smaller in size than the fixed size of the valve passage are inserted, fluid can escape past the smaller size instruments. Universal seals having variable size passages for receiving and sealingly engaging instruments of various sizes have been proposed for endoscopic portals. Many of the universal seals proposed for endoscopic portals are made of elastic, tearable materials, and instruments inserted through the variable size passages come in contact with the tearable materials. Accordingly, there is a risk that the seals may be torn or punctured when instruments are inserted or withdrawn, particularly where the instruments inserted are sharp. In order to avoid tearing by the inserted instruments, more rigid protectors have been disposed within the seals; however, such seals, even with protectors, still have the disadvantages of being opened by contact with an instrument to be introduced and, thus, creating an obstruction to introduction of the instrument and the opportunity for tearing of the seal causing undesirable leakage of gas. Additionally, prior art universal seals increase resistance to introduction and withdrawal of instruments due to contact of the instruments with the seal and can adversely affect the instrument being inserted by such contact.

SUMMARY OF THE INVENTION

Accordingly, it is a primary object of the present invention to overcome the aforementioned disadvantages of prior art endoscopic portals by permitting introduction and withdrawal of instruments with no contact with a seal or valve.

Another object of the present invention is to open a universal seal of an endoscopic portal with a blunt expander such that an instrument can be introduced and/or withdrawn through a variable size passage of the seal without contacting the seal.

A further object of the present invention is to avoid tearing or puncturing a resilient universal seal of an endoscopic portal by opening the resilient seal with a blunt expander such that the expander maintains the seal in an open position and provides a passage for instruments through the seal.

An additional object of the present invention is to provide an endoscopic portal having a universal seal including a seal member and a body of compressible material cooperating to form a seal entirely around the periphery or circumference of an instrument inserted through the seal and having a blunt expander for opening the seal member to receive an instrument.

A further object of the present invention is to utilize a blunt end of an expander to incrementally enlarge a variable size passage of a universal seal to receive an instrument while minimizing fluid flow across the seal.

The present invention has as another object to prevent fluid flow through an endoscopic portal when a universal seal thereof is opened by a tubular expander to receive an instrument.

Yet another object of the present invention is to utilize a valve of an endoscopic portal to prevent fluid flow through the endoscopic portal when a universal seal thereof is opened with a blunt expander to receive an instrument.

Some of the advantages of the present invention are that the universal seals can be utilized in place of conventional trocar or portal valves or in combination with conventional trocar or portal valves, instruments inserted through the universal seals do not present a significant risk of damage to the universal seals since no contact is made by the introduced instruments with the universal seals during insertion, the universal seals can be opened to permit introduction and withdrawal of an instrument without contact adverse to either the instrument or devices or tissue carried by the instrument, opening of the universal seals is easily accomplished, the need for separate protectors in universal seals is eliminated, the universal seals do not have to be completely closed prior to receiving an instrument, the valve passages of valves used with the seals do not have to correspond in size to the size of instruments to be introduced, and the endoscopic portals according to the present invention can be reusable or disposable for single patient use since exposure to bodily fluids and tissue is minimized.

These and other objects, advantages and benefits are realized with the present invention as characterized in an endoscopic portal including a universal seal having a variable size passage for communicating with a body cavity and normally disposed in a closed position wherein the variable size passage has a first cross sectional size. A tubular expander is aligned with the variable size passage and has a cross sectional size larger than the first cross sectional size. The tubular expander has a blunt distal end movable into the variable size passage to move the seal from the normal closed position to an open position wherein the variable size passage has a second cross sectional size larger than the first cross sectional size. The lumen of the tubular expander defines a passage though the seal allowing an instrument having a cross sectional size larger than the first cross sectional size to pass through the lumen of the expander and through the seal. The blunt end of the tubular expander is withdrawable from the variable size passage such that the seal sealingly contacts an instrument therein or returns to the closed position. A method of introducing an instrument at an internal site in the body in endoscopic procedures includes the steps of moving the blunt end of a tubular expander into a variable size passage of a seal to enlarge the variable size passage, introducing an instrument through the lumen of the tubular expander such that the instrument extends through the seal and withdrawing the blunt end of the expander from the variable size passage such that the seal engages the instrument and forms a seal therewith.

Other objects and advantages of the present invention will become apparent from the following description of the preferred embodiments taken in conjunction with the accompanying drawings wherein identical reference numbers indicate identical parts or parts providing identical functions.

BRIEF DESCRIPTION OF THE DRAWINGS

FIG. 1 is a broken perspective view of an endoscopic portal according to the present invention.

FIG. 2 is a broken sectional view of the endoscopic portal showing the universal seal thereof in a closed position.

FIG. 3 is a perspective view of the seal member of the universal seal in the closed position.

FIG. 4 is an end view of the universal seal in the closed position.

FIG. 5 is a broken sectional view of the endoscopic portal showing the universal seal in an open position.

FIG. 6 is a broken sectional view of the endoscopic portal showing the universal seal in a sealing position.

FIG. 7 is an end view of the universal seal in the sealing position forming a seal with an instrument inserted therethrough.

FIG. 8 is a broken sectional view of a modification of an endoscopic portal according to the present invention.

FIG. 9 is an end view of the universal seal for the endoscopic portal of FIG. 8.

FIG. 10 is a broken sectional view of the endoscopic portal of FIG. 8 showing the universal seal in an open position.

FIG. 11 is a broken sectional view of another modification of an endoscopic portal according to the present invention.

FIG. 12 is a side view of the seal member for the universal seal of the endoscopic portal of FIG. 11.

FIG. 13 is a perspective view of the expander for the endoscopic portal of FIG. 11.

FIG. 14 is a broken sectional view of the endoscopic portal of FIG. 11 showing the universal seal in a partially open position.

FIG. 15 is an end view of the seal member in the partially open position.

FIG. 16 is a broken sectional view of the endoscopic portal of FIG. 11 showing the universal seal in a fully open position.

FIG. 17 is an end view of the seal member in the fully open position.

FIG. 18 is a broken sectional view of an additional modification of an endoscopic portal according to the present invention.

FIG. 19 is a perspective view of the universal seal of the endoscopic portal of FIG. 18.

FIG. 20 is a broken sectional view of the endoscopic portal of FIG. 18 showing the universal seal in an open position.

FIG. 21 is a broken sectional view of a further modification of an endoscopic portal according to the present invention.

FIG. 22 is a broken sectional view of the endoscopic portal of FIG. 21 showing the universal seal thereof in an open position.

FIG. 23 is a broken sectional view of yet another modification of an endoscopic portal according to the present invention.

FIG. 32 is a broken sectional view of yet another modification of an endoscopic portal according to the present invention.

FIG. 33 is a broken sectional view of the endoscopic portal of FIG. 32 showing the universal seal thereof in the open position.

FIG. 34 is a broken sectional view of the endoscopic portal of FIG. 32 showing the universal seal in the sealing position.

FIG. 35 is a broken sectional view of an additional modification of an endoscopic portal according to the present invention.

FIG. 36 is a broken sectional view of the endoscopic portal of FIG. 35 showing the universal seal thereof in the open position.

FIG. 37 is a broken sectional view of the endoscopic portal of FIG. 35 showing the universal seal in the sealing position.

FIG. 38 is a sectional view of the universal seal for the endoscopic portal of FIG. 35 in the sealing position.

FIG. 39 is a broken sectional view of a further modification of an endoscopic portal according to the present invention.

FIG. 40 is a perspective view of the universal seal for the endoscopic portal of FIG. 39.

FIG. 41 is a broken sectional view of the endoscopic portal of FIG. 39 showing the universal seal in the open position.

FIG. 42 is a broken perspective view of the universal seal of FIG. 40 in the sealing position.

FIG. 47 is a broken, side sectional view of the endoscopic portal of FIG. 45 showing the valve in the open position and the universal seal in the sealing position forming a seal with the instrument.

FIG. 49 is a broken, side sectional view of a further modification of an endoscopic portal according to the present invention showing both the valve and the universal seal thereof in the closed position.

DESCRIPTION OF THE PREFERRED EMBODIMENTS

Figure 24:
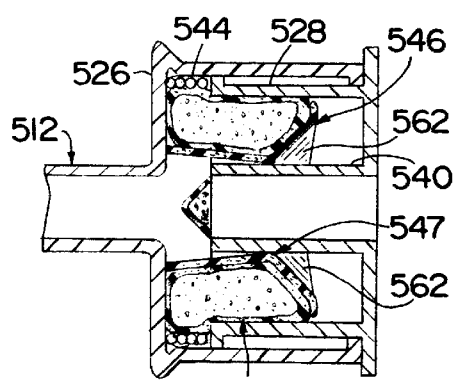
FIG. 24 is a broken sectional view of the endoscopic portal of FIG. 23 showing the universal seal therefor in an open position.

An endoscopic portal 10 according to the present invention is illustrated in FIGS. 1–7. Endoscopic portal 10 includes an elongate tubular member or sleeve 12, a housing 14 mounting a proximal end of tubular member 12 and a universal seal 16 disposed in housing 14. Tubular member 12, which, for example, can take the form of a cannula or portal sleeve or a flexible structure, such as an inflatable membrane, has an open distal end 18 for being disposed at an internal site in a body cavity, an open proximal end 20 for being disposed externally of the cavity and a lumen between the distal and proximal ends. The proximal end 20 is coupled with housing 14 and can be integrally, unitarily formed with a forward wall 30 of housing 14. It should be appreciated, however, that the tubular member can be made separate from the housing and can be coupled with or attached to the housing in many various ways. Where the tubular member is made separately from the housing, the tubular member can be permanently attached to the housing or removably coupled with the housing such as with the use of a threaded connection. Tubular member 12 can be made of any suitable rigid, semi-rigid, flexible or bendable medical grade materials such as metals or plastics as well as flexible, expandable, elastic or stretchable materials such as rubber. The lumen of tubular member 12 has a cross sectional size to receive instruments of various cross sectional sizes. Where the tubular member is made of a rigid material, the lumen can have a fixed cross sectional size to receive instruments having various cross sectional sizes smaller than the cross sectional size of the lumen, or the lumen can have a variable cross sectional size. For example, a longitudinal slit can be provided in the wall of tubular member 12 extending the entire length thereof to permit diametric or cross sectional expansion of tubular member 12 as disclosed in applicant's U.S. Pat. No. 5,429,609 incorporated herein by reference. Where the tubular member is made of a stretchable material, the cross sectional size of the lumen can be variable, with or without a longitudinal slit, due to stretching of the tubular member when instruments having cross sectional sizes larger than the cross sectional size of the lumen are inserted therein. A scale 21 including a plurality of indicia lines is provided along an outer or external surface of tubular member 12. The indicia lines are located predetermined or defined distances from the distal end 18 and from one another allowing scale 21 to be utilized to take measurements in the body. Various numerical indicia can be provided on the outer surface of the tubular member to identify the distances indicated by the indicia lines.

Housing 14 can be made of any suitable material, such as plastic, and can have various configurations including a cylindrical configuration as illustrated in FIG. 1. One or more ports 22 are disposed in housing 14 in communication with the interior thereof; and, preferably, three ports 22 are provided. In the case of endoscopic portal 10, the ports 22 are provided at spaced locations along an enlarged or flared circumferential forward rim 24. The ports 22 can be designed in many various ways to be connectable with one or more supplies of fluid, such as insufflation gases or liquids, to be supplied to the internal site in the body. The ports 22 can be in the nature of stopcocks or pushbutton connectors, for example. Housing 14 includes a cylindrical main body 26 and an end cap 28 slidably mounted to main body 26. Main body 26 includes forward wall 30 and an end wall 32 having an opening therein longitudinally aligned with the lumen of tubular member 12. End wall 32 carries or is formed with an outwardly protruding transverse flange 34 disposed in an open forward end of end cap 28. End cap 28 has a hollow cylindrical configuration terminating distally at an inwardly protruding transverse flange 36 and terminating proximally at a transverse rearward wall 38 having an opening therein aligned with the lumen of tubular member 12. End cap 28 is slidably mounted to a rearward end of main body 26 with flange 34 being retained within the end cap by flange 36. A tubular or hollow expander 40 extends distally from rearward wall 38 and has a lumen aligned with the opening in the rearward wall 38 and aligned with the lumen of tubular member 12. The lumen of expander 40 preferably has a cross sectional size at least as large as the cross sectional size of the lumen of tubular member 12 to receive instruments of various cross sectional sizes. Expander 40 terminates distally at a distal end 42 having a beveled or angled peripheral edge providing a blunt configuration. In the case of endoscopic portal 10, expander 40 is formed integrally, unitarily with rearward wall 38. However, the expander can be a separate component attachable to the end cap in many various ways. A spring or bias member 44 biases the end cap 28 proximally from main body 26 such that housing 14 is normally disposed in a non-compressed condition, position or state with flange 36 in abutment with flange 34. The bias member 44 is in the nature of a coil spring 44 disposed concentrically around expander 40 and mounted between end wall 32 and rearward wall 38. However, it should be appreciated that the bias member can include various types of springs or other bias devices in addition to the coil spring shown as illustrative. End cap 28 is slidable longitudinally along the main body 26 against the bias of spring 44 to move expander 40 distally to a compressed condition, position or state for housing 14 as explained further below. If desired, housing 14 can be provided with a positive stop limiting or controlling distal movement of end cap 28 and, therefore, expander 40, in the compressed condition.

Universal seal 16, which is disposed in main body 26, includes a seal member 46 defining a variable size passage 47 and a compressible member 48 disposed around seal member 46. As best shown in FIG. 3, seal member 46 includes an outwardly protruding, transverse forward or distal flange 50, a hollow conical forward section 52 joined to forward flange 50 and decreasing in cross sectional size in a proximal direction, an intermediate section 54 having an external cylindrical configuration proximally joined to forward section 52, a hollow conical rearward section 56 proximally joined to intermediate section 54 and increasing in cross sectional size in the proximal direction and an outwardly protruding transverse rearward or proximal flange 58 at a proximal end of rearward section 56. A plurality of slits 60 are formed in seal member 46 extending longitudinally from a distal end of the seal member 46 to terminate proximally at slit ends disposed distally or forwardly of rearward flange 58. Preferably, three or four longitudinal slits 60 are formed in the seal member; and, in the case of seal member 46, four slits 60 are formed through the wall of the seal member at 90° spaced locations about a longitudinal axis of the seal member to define four flexible, bendable or resilient legs 62. Seal member 46 is maintained in or internally biased to a closed, initial or contracted position by a spine 64 including a plurality of individual spring wires or stiffeners 64 attached to seal member 46. The spring wires 64 can be disposed on the surface of the seal member or within the material forming the seal member. In the case of seal member 46, the spring wires 64 are disposed within the material of the seal member and extend longitudinally the entire length thereof to establish and/or maintain the configuration of the seal member 46 in the closed position. In the closed position, as shown in FIGS. 2, 3 and 4, legs 62 are biased inwardly toward one another, i.e. in the direction of the longitudinal axis of the seal member 46, such that slits 60 are closed or substantially closed. Longitudinal side edges 65 of legs 62 are close to or in contact with one another such that there are little or no gaps or spaces between legs 62. As shown in FIG. 4, inner surfaces or edges 66 of legs 62 contact one another along intermediate section 54 such that the variable size passage 47 of the seal member 46 is completely closed when the seal member 46 is in the closed position prior to receiving an instrument. Since the variable size passage of seal member 46 is completely closed in the closed position, the seal 16 can be utilized in place of conventional trocar or portal valves to prevent fluid flow through endoscopic portal 10. It should be appreciated, however, that the variable size passage of the seal member does not have to be completely closed in the closed or initial position and that the seal 16 can be utilized with conventional trocar or portal valves, such as flapper and trumpet valves, integrally in housing 14 or as components attachable to housing 14.

Seal member 46 is movable to an open, expanded or second position wherein legs 62 are moved outwardly away from one another, i.e., in a direction transverse to the seal member longitudinal axis, to be spread apart from one another such that the variable size passage 47 is open. The legs 62 are spreadable apart a variable extent or distance such that the passage 47 is of variable cross-sectional size. Seal member 46 is arranged in main body section 26 with rearward flange 58 thereof fixedly received in a recess in end wall 32 and with the variable size passage longitudinally aligned with or in communication with the lumen of tubular member 12. The variable size passage 47 is longitudinally aligned with the lumen of expander 40; and, accordingly, tubular member 12, expander 40 and seal member 46 are coaxially aligned.

Seal member 46 is preferably made of an expandable, stretchable or elastic medical grade material such as Tecoflex manufactured by Thermedics, Inc., Teflon, Goretex or silicone and latex rubbers. However, seal member 46 can be made of various shape memory materials and various spring materials such as stainless steel and titanium. It is desirable for seal member 46 to be made of a tearing-resistant, slippery material. Where the seal member is made of a stretchable, elastic material, no longitudinal slits are necessary as explained hereinbelow. Where no slits are provided in the seal member, a compressible member may not be needed as explained further below. By providing a slitted seal member with an elastic or stretchable inner membrane, a compressible member is not necessary as also explained below. Spring wires 64 can be made of any suitable spring materials such as stainless steel and titanium. However, depending on the materials utilized for the seal member, a separate spine or stiffener may not be needed.

Compressible member 48 includes a body or mass of compressible material 68 disposed around seal member 46 and confined by the main body 26 of housing 14. Compressible member 48 includes a bladder, bag, balloon or membrane 70 made of any suitable expandable, stretchable, elastic, resilient or flexible material forming an envelope for holding compressible material 68 in the interior thereof. It is desirable that membrane 70 be made of a strong, tearing resistant material. Exemplary materials suitable for membrane 70 include Tecoflex, Teflon, Goretex and rubber. Membrane 70 has a toroidal or donut-shape configuration with a central longitudinal passage entirely therethrough. The seal member 46 is disposed in the passage of membrane 70 with forward flange 50 attached to a distal or forward end of membrane 70 and with the slit ends disposed in the membrane passage to be covered by the compressible member 48. The seal member 46 can be attached to the membrane 70 in many various ways including adhesively as in the case of universal seal 16. It should be appreciated that the compressible member can be attached to various parts of the seal member; however, the compressible member does not have to be attached to the seal member. Rather, the compressible member can be attached to the housing 14 instead of the seal member or can be unattached and merely confined by the seal member and/or the housing. Compressible material 68 can be a compressible fluid or a compressible solid material including gases and liquids for exerting a compressive force or pressure on seal member 46. Some suitable compressible materials include air, $CO_2$, nitrous oxide, water, saline, high density liquids such as ADG and Dextran, gel, foam or sponge. The membrane 70 can have various predetermined sizes and configurations to cover any gaps or spaces between legs 62 and/or to grip seal member 46. Exemplary compressible members are disclosed in applicant's U.S. Pat. Nos. 5,389,080 and 5,429,609 incorporated herein by reference. The compressible member can be provided with one or more ports for supplying compressible material to the membrane and/or for removing compressible material from the compressible member such that the compressible member is adjustable in size and sealing force.

It should be appreciated that where the seal member is internally biased to the closed position, external the compressible member 48 need not exert a positive compressive or sealing force against the seal member prior to introduction of an instrument through the variable size passage. However, where a positive compressive or sealing force is exerted by the compressible member against the seal member 46 in the closed position, redundant protection is provided for an enhanced seal. The seal member does not have to be biased to the closed or initial position in that the compressible member can be designed to exert a positive pressure or force on the seal member sufficient to maintain the seal member in the closed position. Where the variable size passage of the seal member is not normally completely closed, due to the seal member not being biased or being insufficiently biased, the compressible member and the force exerted thereby can be utilized to completely close the variable size passage prior to receiving an instrument through the variable size passage. However, as previously noted, the variable size passage does not have to be completely closed in the initial position. It should also be appreciated that the compressible member itself can serve as the seal member with the passage of the compressible member forming the variable size passage. The compressible member can be in the nature of an adjustable, fluid filled balloon to and from which fluid can be supplied; and, since the compressible member is opened by the expander, instruments do not contact the balloon during insertion and/or withdrawal of the instruments.

To use endoscopic portal 10, the distal end 18 of tubular member 12 is disposed at an internal site in the body, and the proximal end 20 of tubular member 12 is disposed externally of the body such that the lumen of tubular member 12 provides a passage or portal establishing communication with the internal site from externally of the body. Tubular member 12 is typically positioned to extend through an anatomical wall W with the use of a penetrating member, such as a trocar or needle, passing through the lumen of tubular member 12 via the seal 16. Introduction of the penetrating member through seal 16 is accomplished in the same manner as described hereinafter for introduction of various size instruments through the endoscopic portal. The penetrating member is utilized to penetrate the anatomical wall W allowing the tubular member 12 to follow the penetrating member through the anatomical wall. Once the tubular member 12 has been positioned to extend through the anatomical wall, the penetrating member is withdrawn from the endoscopic portal 10 leaving the tubular member 12 in place. Withdrawal of the penetrating member from endoscopic portal 10 causes the seal member 46 to automatically return to the closed position shown in FIG. 2. With seal member 46 disposed in the closed position, the inner surfaces 66 of seal member 46 along intermediate section 54 are in contact with one another such that the variable size passage 47 is completely closed. Housing 14 will be in a non-compressed or rest state or condition with spring 44 biasing end cap 28 proximally from main body section 26. With the end cap 28 biased from main body section 26, the distal end 42 of expander 40 will be withdrawn from or disposed proximally of intermediate section 54 of seal member 46 such that the variable size passage 47 along intermediate section 54 remains closed. The expander 40 extends distally through the opening in end wall 32; and, in the case of endoscopic portal 10, the angled peripheral edge at the distal end 42 of expander 40 is disposed slightly within the rearward section 56 of seal member 46 with the angled peripheral edge in contact with the sloping wall of rearward section 56. Compressible member 48 is disposed over slits 60; and, in the case of seal 16, exerts a closing force or positive pressure on seal member 46. Various fluids, such as insufflation gases, can be introduced at the internal site via the ports 22, which are in fluid communication with the lumen of tubular member 12 since the universal seal 16 is spaced proximally from the forward wall 30 of main body section 26.

When it is desired to introduce an instrument at the internal site through the endoscopic portal 10, housing 14 is squeezed or compressed, moving end cap 28 longitudinally, distally relative to the main body 26 against the bias of spring 44. Housing 14 will be in a compressed state or condition as shown in FIG. 5, and expander 40 will be moved longitudinally, distally into variable size passage 47. The expander 40 overcomes the closing force or bias of seal member 46 and the compressive force of compressible member 48 to spread legs 62 apart from one another as facilitated by the angled peripheral edge of expander 40 in contact with the inner surface of seal member 46. The legs 62 are moved outwardly by expander 40 in a direction transverse or radial to a longitudinal axis of endoscopic portal 10 causing the seal member 46 to be moved from the closed position wherein the variable size passage has a first cross sectional size to an open position wherein the variable size passage has a second cross sectional size larger than the first cross sectional size. Once the distal end 42 of expander 40 has entered forward section 52 of seal member 46, the seal member will be in a fully open position as shown in FIG. 5. In the open position, side edges 65 of legs 62 are spaced further apart from one another, and the seal member is biased toward the closed position such that inner surfaces 66 are in contact with the outer surface of expander 40 along intermediate section 54. Movement of seal member 46 to the open position compresses compressible member 48 which exerts an increased compressive force against the seal member 46 since the compressible member 48 is confined by the seal member 46 and the housing 14. Therefore, the seal 16 forms a seal with the expander 40 due to the closing force or bias of the seal member 46 and the compressive force of compressible member 48, which fills the gaps or spaces between legs 62 as explained further below. Since the seal 16 is opened by a blunt expander, tearing, puncturing and other damage to components of the seal is avoided. The lumen of expander 40 provides a passage through the seal member 46 such that instruments having various cross sectional sizes larger than the first cross sectional size can be inserted in variable size passage 47 without coming into contact with the seal 16 and without resistance to insertion which would otherwise be presented by the seal. With the seal 16 maintained in the open position, an instrument I having a cross sectional size the same as or smaller than the cross sectional size of the lumen of expander 40 is inserted through the lumen of expander 40 into the lumen of tubular member 12 such that the instrument extends through seal 16. End cap 28 is released allowing the housing 14 to automatically return to the non-compressed state with expander 40 being withdrawn from the variable size passage 47. Once the housing 14 has returned to the non-compressed state, the universal seal 16 will be in a sealing position with seal member 46 urged toward the closed position by spine 64 as well as by compressible member 48 exerting a compressive sealing force or pressure on seal member 46. As shown in FIGS. 6 and 7, the compressible member 48 occupies or fills the gaps or spaces between legs 62 and sealingly contacts the outer surface of instrument I between legs 62 to complete the seal entirely along the circumference or periphery of instrument I. Accordingly, universal seal 16 engages the instrument I to form a seal therewith while allowing the instrument I to be moved longitudinally through the variable size passage 47. To slidably withdraw instrument I from endoscopic portal 10, housing 14 is squeezed causing expander 40 to enter variable size passage 47 to be disposed between the instrument I and the seal member 46. The instrument I can then be withdrawn through the expander 40 without contacting the universal seal. Once the instrument I is withdrawn and the housing 14 is released, the universal seal 16 will automatically return to the closed or initial position. It should be appreciated that since the instrument I is slidably disposed in the variable size passage, the instrument can be withdrawn from the seal without enlarging the variable size passage utilizing the expander. However, withdrawal of instrument I through the lumen of the expander has the advantage of eliminating contact by the instrument with the seal as well as eliminating resistance to withdrawal.

Another embodiment of an endoscopic portal according to the present invention is illustrated at 110 in FIG. 8. Endoscopic portal 110 is similar to endoscopic portal 10 except that seal member 146 of universal seal 116 for endoscopic portal 110 includes multiple layers and except that bias member 144 for end cap 128 of endoscopic portal 110 includes a pair of springs 144 on opposite sides of expander 140. Universal seal 116 includes seal member 146 made up of inner and outer seal members 146A and 146B, respectively, and compressible member 148 disposed around the outer seal member 146B. Seal members 146A and 146B have forward sections 152A and 152B, respectively, rearward sections 156A and 156B, respectively, and transverse rearward flanges 158A and 158B, respectively, fixedly secured in a recess in end wall 132 of main body 126 of housing 114. Forward sections 152A and 152B have cylindrical external configurations of uniform cross section from distal ends of the seal members 146A and 146B, respectively, to rearward sections 156A and 156B, respectively. Rearward sections 156A and 156B have hollow conical configurations with cross sections of increasing size from forward sections 152A and 152B, respectively, to rearward flanges 158A and 158B, respectively. The seal member 146A is arranged or disposed within seal member 146B in nesting arrangement with distal ends of the seal members 146A and 146B, respectively, in alignment with one another and with rearward flanges 158A and 158B in overlapping engagement. Accordingly, the seal members 146A and 146B form a double layer seal member 146, and the seal members 146A and 146B can be connected or attached to one another or can remain separate or unattached from one another. In the case of endoscopic portal 110, the seal members 146A and 146B are not connected to one another but are held together with a snug or frictional fit and/or by retention of rearward flanges 158A and 158B in end wall 132. Where the seal members are connected to one another, the seal members can be connected in many various ways such as adhesively or with the use of mechanical components. Seal members 146A and 146B have longitudinally extending slits 160 defining a plurality of legs. As shown in FIG. 9, each seal member 146A and 146B has four slits at 90° spaced locations with slits 160A of seal member 146A being offset from or not aligned with slits 160B of seal member 146B. In the case of seal member 146, each slit 160A is disposed between two adjacent slits 160B. Accordingly, each seal member 146A and 146B includes four resilient legs 162A and 162B, respectively, and longitudinal spring wires extend longitudinally along the legs within the thickness of the walls of the seal members as described for seal member 46. The seal member 146 is normally disposed in a closed position with the legs of each seal member 146A and 146B biased inwardly toward one another. In the closed position, internal surfaces 166A of the legs of seal member 146A are close to one another along forward section 152A such that the variable size passage 147 through seal 146 is substantially closed to block the lumen of tubular member 112. Outer seal member 146B grips inner seal member 146A, and the legs 162B of outer seal member 146B cover the slits 160A of inner seal member 146A. Compressible member 148 is disposed over seal member 146, with the slits 160B of outer seal member 146B being covered by the compressible member. Springs 144 bias end cap 128 proximally from the main body 126 such that a blunt, angled peripheral edge at a distal end of expander 140 is disposed slightly within rearward section 156A but does not exert an opening, expanding or spreading force on the seal member 146 such that the universal seal 116 remains in the closed position as shown in FIG. 8.

Use of endoscopic portal 110 is similar to that described above in that housing 114 is compressed against the bias of springs 144. As shown in FIG. 10, compression of housing 114 causes expander 140 to move further into seal member 146 to enter variable size passage 147 and move the legs of the seal members 146A and 146B in an outward direction as facilitated by movement of the angled peripheral edge of the expander 140 along the angled inner surface of rearward section 156A. Once the distal end 142 of expander 140 is disposed in variable size passage 147, the universal seal 116 will be in an open position as shown in FIG. 10 allowing an instrument to be inserted through the expander 140 into the lumen of tubular member 112 without contacting the seal 116. Upon release of housing 114 and return thereof to the non-compressed condition, the seal member 146 will be in a sealing position and will exert a sealing force on the inserted instrument due to the closing force of the seal member 146 as well as the compressive force of compressible member 148, and the compressible member 148 will fill the spaces between the legs of seal member 146B to form a fluid tight seal with the inserted instrument. Since the variable size passage 147 is not completely closed in the closed or initial position, endoscopic portal 110 can be provided with a conventional valve distally of seal 116 to prevent fluid flow to and from the internal site in the body. Where such valve is provided distally of seal 116, the instrument is inserted through the valve subsequent to insertion through the universal seal such that a seal is formed with the instrument prior to opening the valve.

Another embodiment of an endoscopic portal according to the present invention is illustrated in FIG. 11 at 210. Endoscopic portal 210 is similar to endoscopic portal 10 except that universal seal 216 for endoscopic portal 210 includes a "duck bill" type seal member 246 and except that end cap 228 for endoscopic portal 210 is biased by two springs 244 and includes a removable expander 240 having distally protruding prongs 272. As best shown in FIG. 12, seal member 246 includes a forward section 252 of uniform cross section proximally joined to rearward section 256 which, in turn, terminates proximally at transverse rearward flange 258 secured in end wall 232 of main body section 226 of housing 214. Forward section 252 has side walls 273 normally disposed in contact with one another in a closed or initial position for seal member 246. Rearward section 256 has a hollow, semi-spherical or dome-like external shape with a cross-section increasing in size from forward section 252 to rearward flange 258. Spring wires 264 extend longitudinally the entire length of seal member 246 and, provide seal 246 with a shape memory which alone or in combination with compressible member 248, maintain the seal member 246 in the closed position wherein variable size passage 247 along the length of forward section 252 is closed. As best shown in FIG. 13, expander 240 has a tubular body extending distally from a transverse flange 274 and a pair of prongs 272 extending distally from the tubular body. Prongs 272 extend inwardly toward one another in the direction of a longitudinal axis of expander 240, and each prong 272 has a lobed configuration with a rounded, distally protruding central lobe or finger 275 aligned with a longitudinal axis of the expander and two lateral lobes or bumps 276 disposed proximally of central finger 275 and on opposite sides thereof. Flange 274 has an opening therein communicating with the lumen of expander 248 and has a thread 277 along the periphery thereof to threadedly engage a corresponding thread on end cap 228, with the flange 274 completing the rearward wall of housing 214. The expander 240 is arranged in housing 214 such that the distance between the lateral lobes 276 of a prong 272 extends in the same direction as side walls 273, i.e. in the same direction as the major dimension of the cross section of forward section 252. With the end cap 228 biased by springs 244 in the non-compressed condition for housing 214, prongs 272 are disposed in rearward section 256 of seal member 246 with lateral lobes 276 in contact with an internal surface of the seal member 246; however, the expander 240 does not protrude into the forward section 252 of seal member 246 such that the variable size passage 247 remains closed. Compressible member 248 is disposed around the forward section 252 and part of rearward section 256.

Use of endoscopic portal 210 is similar to that described above in that housing 214 is compressed causing expander 240 to be moved into the variable size passage 247 such that the central lobe 275 enters the forward section 252 to partially open the universal seal 216 as shown in FIG. 14. As shown in FIG. 15, central lobe 275 entering forward section 252 causes the seal member to move to a partially open position wherein a central passage 247 of circular or oval cross section is defined through seal member 246. In the partially open position, outer portions of the opposing side walls 273 remain in contact with one another to minimize the size of passage 247 and to thusly minimize leakage across 11 seal 216. Accordingly, an instrument having a cross sectional size smaller than the cross sectional size of passage 247 in the partially open position can be introduced in the lumen of tubular member 212 without opening the seal 216 larger than necessary. It should be appreciated that the lobe or protrusion can be designed to extend the length of passage 247 such that an instrument can be inserted through the expander 240 without contacting the seal 216 when the seal is in the partially open position. As shown in FIGS. 16 and 17, further compression of housing 214 causes the lateral lobes 276 to enter forward section 252 such that the seal member 246 is in a fully open position with the variable size passage 247 being open to a circular cross sectional size larger in size than the cross sectional size of the passage in the partially open position. Accordingly, it should be appreciated that the universal seals according to the present invention can be opened gradually or incrementally between the closed position and the fully open position and that smaller size instruments can be introduced through the seals when the seals are in the partially open positions. It should also be appreciated that the universal seals can be designed such that the variable size passage has a configuration in the partially open position to permit introduction of instruments therethrough while minimizing fluid flow and, in particular, the leakage or desufflation of gas, across the seals. Where the seal member 246 has a bias or shape memory sufficiently strong to maintain the seal member in the closed position and to form a seal with inserted instruments, the compressible member 248 is not necessary.

FIG. 18 illustrates at 310 an additional embodiment of an endoscopic portal according to the present invention. Endoscopic portal 31 includes universal seal 316 having a seal member 346 but no compressible member. As shown in FIG. 19, seal member 346 has a forward section 352 having a hollow conical configuration with a cross section of increasing size from a distal end of the seal member to a rearward flange 358 proximally joined to forward section 352. Rearward flange 358 is fixedly secured in end wall 332 of main body 326 of housing 314. The seal member 346 is made entirely of elastic or stretchable material and is normally disposed in a closed position as shown in FIG. 18 wherein the variable size passage 347 at a distal end or tip of the seal member is is closed to block communication with the lumen of tubular member 312. Housing 314 is normally disposed in the non-compressed condition with springs 344 biasing end cap 328 proximally from main body 326. In the non-compressed condition, the expander 340 protrudes into the forward section 352 such that the blunt distal end 342 thereof is in contact with the internal surface of seal member 346 while the seal member remains in the closed position. When housing 314 is squeezed or compressed as illustrated in FIG. 20, expander 340 is moved distally into the seal member 346 causing the seal member 346 to stretch or expand to conform to the outer configuration of the expander. Accordingly, expander 340 opens variable size passage 347 allowing an instrument to be introduced through the lumen of the expander into the lumen of tubular member 312. When the housing 314 is allowed to return to the non-compressed condition, the seal member 346 will be disposed in sealing contact with the introduced instrument due to stretching of the seal member since the cross sectional size of the instrument is larger than the cross sectional size of the variable size passage 347 in the closed position.

Another embodiment of an endoscopic portal according to the present invention is illustrated in FIG. 21 at 410. Endoscopic portal 410 is similar to endoscopic portal 10 except that universal seal 416 for endoscopic portal 410 includes an accordion type or corrugated seal member 446. Seal member 446 includes a forward section 452, an intermediate section 454 proximally joined to forward section 452, a rearward section 456 proximally joined to intermediate section 454 and a rearward flange 458 proximally joined to rearward section 456 and secured in end wall 432 of the main body section 426 of housing 414. Forward section 452 has a hollow conical configuration with a cross section decreasing in size in the proximal direction. Intermediate section 454 has a hollow configuration with a circular cross section increasing in size from forward section 452 to an apex 480 and a circular cross section decreasing in size from apex 480 to rearward section 456. Rearward section 456 has a hollow, truncated conical configuration with a cross section increasing in size from intermediate section 454 to rearward flange 458. Seal member 446 has slits 460 at 90° spaced locations to define four legs 462, and a plurality of spring wires (not shown) extend longitudinally along the legs such that the seal member 446 is normally in a closed position with internal surfaces 466 of the legs in contact with one another at the junction of forward section 452 with intermediate section 454. Accordingly, the variable size passage 447 at the junction is closed such that no fluid can pass through the universal seal 416. Compressible member 448 is disposed around seal member 446 and is confined by the main body section 426 of housing 414. End cap 428 and expander 440 for endoscopic portal 410 are similar to those of endoscopic portal 10; and, when the housing 414 is in the non-compressed condition, the distal end 442 of expander 440 protrudes slightly into the rearward section 456 of seal member 446 such that the angled distal edge of the expander is in contact with the internal wall of the seal member.

Use of endoscopic portal 410 is similar to that previously described in that housing 414 is squeezed or compressed causing expander 440 to be moved distally into the variable size passage 447 causing the legs 462 of the seal member to be moved radially outwardly or spread apart from one another. With the housing 414 in a fully compressed condition, the universal seal 416 will be in a fully open position with the lumen of expander is 440 providing a passage through the seal member as shown in FIG. 22. The closing force of the seal member 446 as well as the compressive force of the compressible member 448 causes the seal member 446 to seal against the expander 440 at the junction of the forward section 452 with the intermediate section 454 and at the junction of the intermediate section 454 with the rearward section 456. In addition, the compressible member 448 fills the spaces between legs 462. After an instrument is introduced through the expander 440 into the lumen of member 412 and the housing 414 is allowed to return to the non-compressed condition, the seal member 446 will be urged into contact with the instrument to form a seal with the instrument as described above for the seal formed with the expander 410.

Another embodiment of an endoscopic portal is illustrated in FIG. 23 at 510. Endoscopic portal 510 is different from endoscopic portal 10 in that the universal seal 516 for endoscopic portal 510 is disposed partly within end cap 528 with seal member 546 thereof secured to forward wall 530 of housing 514, and the forward end of end cap 528 is disposed within the rearward end of the housing main body 526 with spring 544 disposed around the universal seal 516. Universal seal 516 is similar to universal seal 16 and includes seal member 546 and compressible member 548 disposed around seal member 546. Seal member 546 is essentially the same as seal member 40 except that a distal end of seal member 546 is fixedly secured to forward wall 530 of main body 526. The rearward flange 558 of the seal member 546 is disposed in end cap 528. An outwardly protruding flange 534 at the forward end of end cap 528 is disposed in the main body 526 and is held therein by an inwardly protruding flange 536 at an open rearward end of main body 526. Spring 544 is disposed between the forward wall 530 and the flange 534 to bias the end cap 528 proximally from the main body 526 in a non-compressed state for housing 514. Spring 544 is a helical coil spring disposed around compressible member 548; however, various other types of springs or bias members and arrangements therefor can be utilized in the endoscopic portals of the present invention. Expander 540 protrudes distally from rearward wall 538, and the distal end 542 of the expander is disposed slightly in rearward section 556 in the non-compressed state.

Use of endoscopic portal 510 is similar to that previously described in that housing 514 is squeezed to move expander 540 into the variable size passage 547. As shown in FIG. 24, movement of expander 540 further into seal member 546 causes the legs 562 of the seal member to be spread apart such that the universal seal 516 is opened by the expander 540 allowing an instrument to be introduced through the lumen of the expander 540 into the lumen of tubular member 512. Once the instrument has been inserted through the universal seal 516, the housing 514 is released; and, upon return of the housing 514 to the non-compressed state, the universal seal 516 will create a seal with the inserted instrument as explained above.

Figure 25:
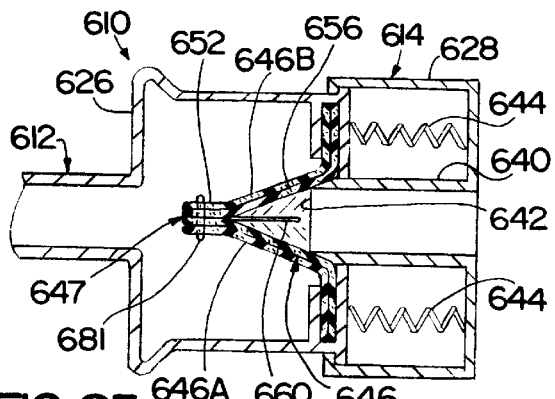
FIG. 25 is a broken sectional view of still a further modification of an endoscopic portal according to the present invention.

A still further embodiment of an endoscopic portal according to the present invention is illustrated at 610 in FIG. 25. Endoscopic portal 610 is similar to endoscopic portal 110 and includes seal member 646 having inner and outer seal members 646A and 646B, respectively; however, seal member 646 includes an elastic or stretchable ring or band 681, serving as a compressible member disposed around the forward section 652 of seal member 646. In the case of seal member 646, the inner seal member 646A has four longitudinal slits 660 defining four legs and the outer seal member 646B does not have any slits. The slits of the inner seal member 646A are covered by the outer seal member 646B. Ring 681 is snugly or tightly disposed around outer seal member 646B to bias the seal member 646 to a closed position wherein inner surfaces of the legs of inner seal member 646A are in contact with one another such that the variable size passage 647 along the forward section 652 of the seal member is closed. Ring 681 can be made of any suitable elastic, stretchable or expandable material such as stretchable or elastic rubber or metal. The housing 614 for endoscopic portal 610 is normally disposed in the non-compressed state with end cap 628 biased proximally from the main body 626 by springs 644 and with the distal end 642 of expander 640 disposed in contact with an internal wall of rearward section 656.

Figure 26:
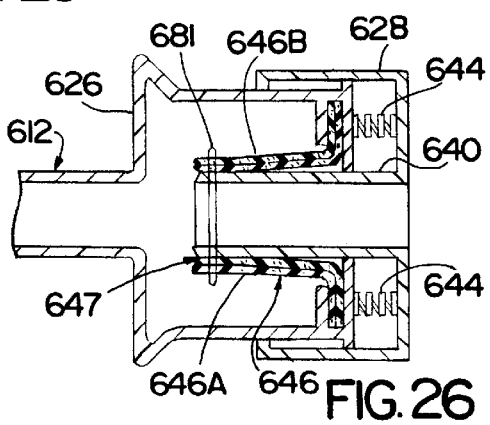
FIG. 26 is a broken sectional view of the endoscopic portal of FIG. 25 showing the universal seal therefor in the open position.

Use of endoscopic portal 610 is similar to that described above in that movement of expander 640 further into seal member 646 via squeezing operation of housing 614 causes the legs of the inner seal member 646A to be moved or spread outwardly as permitted due to stretching of outer seal member 646B and ring 681 as shown in FIG. 26. Accordingly, the universal seal 616 is opened by expander 640 allowing an instrument to be introduced through the lumen of the expander into the lumen of tubular member 612. Upon release of housing 614, the seal member 646 will form a seal with the inserted instrument due to the closing or sealing force of the inner seal member 646A, the outer seal member 646B and/or the compressive force of ring 681.

Figure 27:
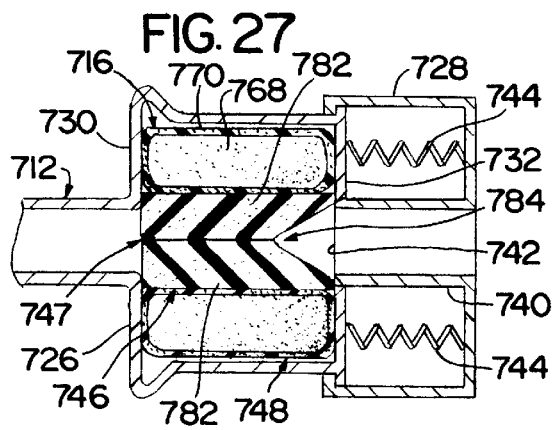
FIG. 27 is a broken sectional view of an additional modification of an endoscopic portal according to the present invention.
Figure 28:
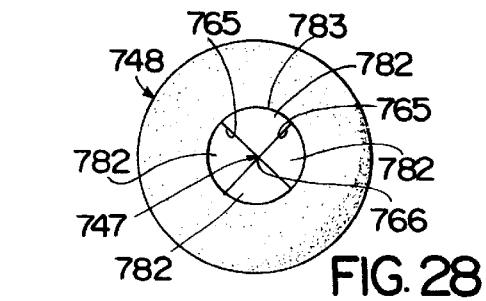
FIG. 28 is an end view of the universal seal for the endoscopic portal of FIG. 27 showing the universal seal in the closed position.

Another embodiment of an endoscopic portal according to the present invention is illustrated at 710 in FIG. 27. Endoscopic portal 710 includes a universal seal 716 having a seal member 746 and a compressible member 748. Seal member 746 is made up of a plurality, preferably three or more, block members 782 disposed in the passage of compressible member 748. As shown in FIG. 28, seal member 746 includes four solid block members 782 each having a curved outer surface 783 defining an arc of 90° and straight side surfaces 765 converging at an inner edge or surface 766 to define a one-quarter segment of a cylinder. A conical passage or recess 784 is formed in a proximal end of the seal member 746, the passage 784 having a cross section decreasing in size in the distal direction. Accordingly, each block member 782 has a segment removed therefrom corresponding to one-quarter of the conical passage. The block members can be made of various materials including rubber. Seal member 746 has a length such that a distal end of each block member 782 abuts the forward wall 730 of the housing main body 726, and a proximal end of each block member 782 abuts the end wall 732 for confinement against longitudinal movement. Compressible member 748 is disposed around the seal member 746 and includes a bladder or membrane 770 filled with a compressible sponge material 768. Various sponge materials can be utilized in compressible member 748 including polyvinyl alcohol sponge, foam rubber, compressed cellulose sponge, natural sponge, synthetic sponge, polyurethane foam, gauze and cotton. Depending on the sponge material utilized, membrane 770 may not be necessary. In addition to the sponge material, the compressible member 748 can contain a fluid for wetting the sponge; however, depending on the sponge material utilized, a wetting fluid may not be necessary. The block members 782 can be attached to the compressible member 748, or the block members 782 can be unattached and held within the passage of the compressible member 748 due to the compressive force thereof. The compressible member 748 maintains or biases the seal member 746 in a closed position wherein side surfaces 765 of adjacent block members 782 and inner surfaces 766 are in contact with one another. In the closed position as shown in FIG. 28, no spaces exist between adjacent blocks 782 such that the variable size passage 747 is closed. End cap 728, expander 740 and springs 744 for endoscopic portal 710 are essentially the same as those for endoscopic portal 110; and, when housing 714 is in a non-compressed state, the distal end 742 of expander 740 is disposed slightly in the tapered passage 784 of the seal member 746 with the angled peripheral edge of the expander 740 in abutment with the sloping or angled walls of block members 782 defining the passage 784.

Figure 29:
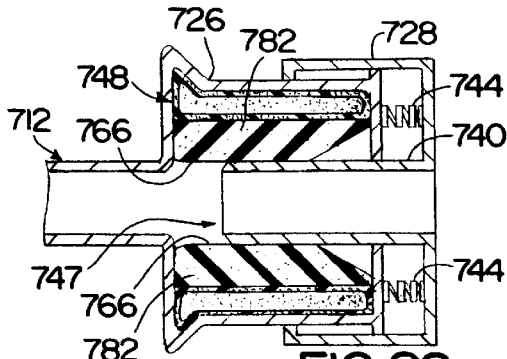
FIG. 29 is a broken sectional view of the endoscopic portal of FIG. 27 showing the universal seal in the open position.
Figure 31:
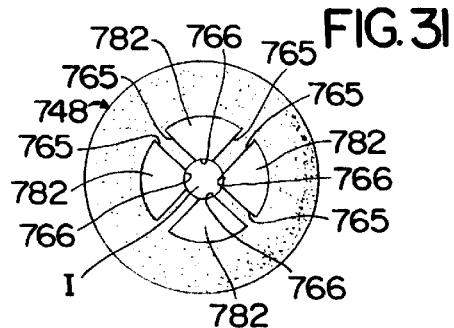
FIG. 31 is an end view of the universal seal for the endoscopic portal of FIG. 27 showing the universal seal in the sealing position.
Figure 30:
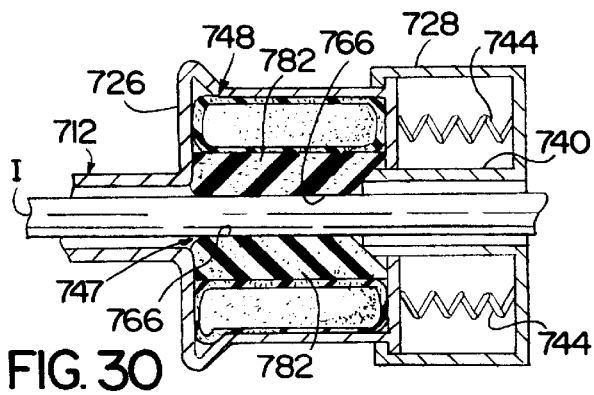
FIG. 30 is a broken sectional view of the endoscopic portal of FIG. 27 showing the universal seal in a sealing position.

During use of endoscopic portal 710, the housing 714 is compressed to move expander 740 further into the seal member 746 causing block members 782 to be moved outwardly away from one another in a direction transverse or radial to a longitudinal axis of portal 710. Movement of block members 782 outwardly is facilitated by engagement of the angled peripheral edge of expander 740 with the angled walls of the block members 782, and the variable size passage 747 will be opened gradually. Continued movement of expander 740 further into seal member 746 causes the expander to enter variable size passage 747 with the outer surface of the expander sliding along the internal surfaces 766 of the block members 782 for movement of the seal member to the fully open position as shown in FIG. 29. An instrument I is inserted through the expander 740 into the lumen of tubular member 712, and the housing 714 is released for return to the non-compressed condition as shown in FIG. 30. The universal seal 716 forms a seal with the inserted instrument I due to the internal surfaces 766 of the block members being urged into engagement with the outer surface of instrument I and due to the compressible member 748 filling the spaces, gaps or interstices between the block members 782 as shown in FIG. 31. Accordingly, the compressible member 748 contacts the outer surface of instrument I between the block members completing a seal extending along the entire periphery or circumference of instrument I. Since the block members 762 are made of rubber, the internal surfaces 766 are somewhat flattened in the open position to seal against instrument I.

FIG. 32 illustrates at 810 another embodiment of an endoscopic portal according to the present invention. Endoscopic portal 810 is similar to endoscopic portal 710 except that universal seal 816 for endoscopic portal 810 utilizes springs 885 as the compressible member. Universal seal 816 includes four block members 882, similar to block members 782, and compressible members 848 including a spring 885 for each block member 882. Springs 885, two of which are seen in FIG. 32, are helical coil springs disposed between outer surfaces 883 of block members 882 and side walls 886 of housing main body 826. Springs 885 apply a compressive or sealing force to block members 882, urging the block members inwardly toward one another, i.e. in the direction of a longitudinal axis of endoscopic portal 810, to cause the block members 882 to be normally disposed in a closed position as shown in FIG. 32 wherein variable size passage 847 is closed. When expander 840 is moved distally between block members 882 via squeezing of housing 814, the block members 882 are moved outwardly away from one another in a direction radial or transverse to the longitudinal axis. As shown in FIG. 33, expander 840 moves seal member 846 to open variable size passage 847 allowing an instrument I to be introduced in the lumen of tubular member 812 while the springs 885 urge block members 882 into contact with expander 840 to maintain a seal therewith. Upon return of housing 814 to the non-compressed condition, the block members 882 form a seal with the introduced instrument I due to the compressive sealing force of springs 885 as shown in FIG. 34. The seal member 846 can be provided with a stretchable membrane between inner surfaces 866 of block members 882 to sealingly contact the instrument I and bridge the gaps between the block members 882 as described below for seal member 946.

Another modification of an endoscopic portal according to the present invention is illustrated at 910 in FIG. 35. Endoscopic portal 910 incorporates a universal seal 916 similar to universal seal 16 except that universal seal 916 includes an elastic ring 981 as the compressible member and has a stretchable or elastic layer or membrane 987 along the internal surface of seal member 946. The seal member 946 is similar to seal member 46 and includes four slits defining four legs. Membrane 987 is disposed on an inner surface of seal member 946 to cover the slits. In the case of seal member 946, membrane 987 is attached to the seal member 946 and extends entirely along the inner surface from a distal end of seal member 946 to rearward flange 958. The membrane 987 can be made of various elastic or stretchable materials as described previously herein and preferably is made of a slippery, tearing-resistant material. Elastic ring 981 is disposed around intermediate section 954 of the seal member and biases the seal member toward a closed position wherein the variable size passage 947 is closed as shown in FIG. 35.

Use of endoscopic portal 910 is similar to that described above in that housing 914 is compressed causing expander 940 to be moved distally into the variable size passage 947 causing the legs 962 to be spread outwardly to an open position as permitted due to stretching of ring 981 as shown in FIG. 36. With the seal in the open position, an instrument I is inserted through the lumen of expander 940 into the lumen of tubular member 912. Upon release of housing 914 and return thereof to the non-compressed state, elastic ring 981 applies a compressive sealing force to the legs of the seal member causing the legs to form a seal with instrument I as shown in FIG. 37. The membrane 987 stretches or expands between the legs 962 of the seal member to conform to and contact the periphery of instrument I, and the membrane connected between legs 962 bridges the spaces or interstices between the legs 962 of the seal member to form a seal entirely around the circumference or periphery of instrument I as shown in FIG. 38 for intermediate section 954.

A further modification of an endoscopic portal according to the present invention is illustrated at 1010 in FIG. 39. Endoscopic portal 1010 is similar to endoscopic portal 310 except that universal seal 1016 for endoscopic portal 1010 includes seal member 1046 comprising an involuted conical body formed of a resilient material rolled into a spiral as shown in FIGS. 39 and 40, rearward flanges 1058A and 1058B extend transversely from angularly spaced locations along a proximal edge of the involuted cone for being received in recesses in end wall 1032 of main body 1026. Flange 1058A is connected near an outer lateral edge 1089 of the cone, and flange 1058B is connected near an inner lateral edge so that the flanges are rotatable relative to one another to roll or unroll the cone. The involuted overlapping surfaces of the cone are preferably in sliding contact with one another to maintain a seal along the length of the seal member 1046 and are biased into the spiral shapes shown, for example by fabricating the cone of resilient materials and/or by using imbedded circular spring members 1064 spaced longitudinally along the length of the cone. Variable size passage 1047 at the distal end of the cone is formed by mating contact between the rolled distal edges of the cone and is normally closed to form a seal. In the non-compressed condition for housing 1014 of endoscopic portal 1010, flanges 1058A and 1058B are movably held in the end wall 1032 and there is a gap or space between the cone and the end wall 1032 to accommodate expansion of seal 1046. End cap 1028 is biased proximally from main body 1026 by spring 1044 with the distal end 1042 of expander 1040 disposed slightly within the cone. In use, housing 1014 is compressed causing expander 1040 to be moved distally into seal member 1046 such that the cone resiliently unfurls to increase the size of the variable size passage 1047 as shown in FIG. 41. Thus, when the expander 1040 contacts the cone, the walls of the cone will unfurl until the variable size passage 1047 is open to accommodate expander 1040. The cone can be made of resilient material and/or spring biased to the coiled condition such that the seal tends to close against the expander 1040 forming a seal. An instrument can then be inserted through the lumen of expander 1040 into the lumen of tubular member 1012; and, when the housing 1014 is released for return to the non-compressed condition, the inner surface of the cone will be in contact with the instrument I to form a seal therewith as shown in FIG. 42.

Figure 43:
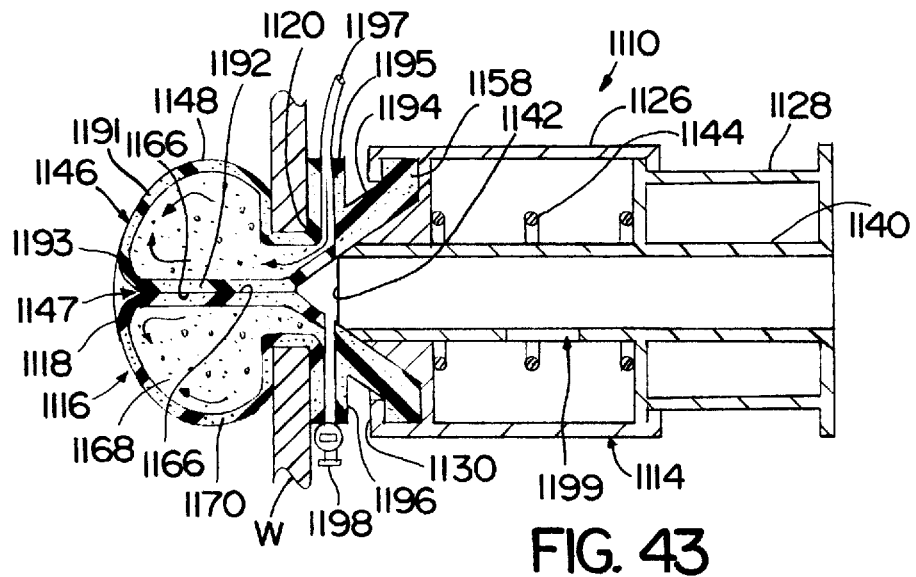
FIG. 43 is a broken sectional view of yet another modification of an endoscopic portal according to the present invention.

Yet another modification of an endoscopic portal according to the present invention is illustrated at 1110 in FIG. 43. Endoscopic portal 1110 is representative of an endoscopic portal wherein the universal seal itself forms a portal establishing communication with a body cavity. Endoscopic portal 1110 includes universal seal 1116 having a seal member 1146. Seal member 146 is formed by compressible member 1148 comprising a bladder, bag or balloon for holding compressible material 1168. Compressible member 1148 includes a stretchable or elastic membrane 1170 having a membrane outer wall 1191 connected to a membrane inner wall 1192 by a membrane distal end wall 1193. The seal member 1146 has a distal end 1118 for being disposed in a body cavity, a proximal end 1120 for being disposed externally of the body cavity and a variable size passage 1147 between the distal and proximal ends. The variable size passage 1147 extends through the compressible member 1148; and, when membrane 1170 is filled with compressible material 1168, surfaces 1166 of the membrane inner wall 1192 are in contact with one another at which time the variable size passage 1147 will be closed in the closed or initial position. The proximal end 1120 of compressible member 1148 is connected to a neck 1194 having a truncated conical external configuration with a cross section increasing in size in the proximal direction. Neck 1194 is preferably made of a deformable or resilient material such as rubber and terminates proximally at a rearward or proximal flange 1158 secured in a recess in a forward wall 1130 of main body 1126 of housing 1114. Neck 1194 carries or forms fluid ports 1195 and 1196 disposed distally of rearward flange 1158. Fluid port 1195 is preferably made of a rigidified or non-elastic, non-stretchable material and is of hollow construction or formed with a passage or channel therein. Fluid port 1195 extends transversely from the proximal end 20 of compressible member 1148 with an inner end thereof connected to the membrane outer wall 1191 and to a distal end of neck 1194. The membrane inner wall 1192 is connected to the distal end of neck 1194 such that the hollow interior or passage of fluid port 1195 is in fluid communication with the interior of membrane 1170. Fluid port 1196 is similar to fluid port 1195 except that the passage or channel thereof does not communicate fluidically with the interior of membrane 1170 but, rather, with the passage 1147 of the compressible member 1148. Fluid port 1195 is connectable with a source or supply of compressible fluid material; and, as shown in FIG. 43, a tube or conduit 1197 is connected to fluid port 1195 for supplying a fluidic compressible material to the interior of membrane 1170. Fluid port 1195 can be provided with a valve for controlling the supply of fluid to the interior of membrane 1170, and fluid can be withdrawn from membrane 1170 via the fluid port 1195 such that the compressible member 1148 is adjustable during use. Fluid port 1196 is provided with a valve such as a stopcock 1198 and is connectable with a source of fluid, such as insufflation gas, to be introduced in the body cavity. Housing 1114, which is similar to housing 514, includes main body 1126 and end cap 1128. Tubular expander 1140 is carried by end cap 1128, and the end cap 1128 is biased proximally from the main body 1126 by spring 1144. With the end cap 1128 biased proximally from main body 1126 in a non-compressed condition for housing 1114, the distal end 1142 of expander 1140 is disposed in an internal conical or tapered recess defined in neck 1194. It should be appreciated that the membrane can be attached or connected to the neck 1194 and/or the fluid ports 1195 and 1196 in many various ways including adhesively and being formed integrally, unitarily with the neck and/or fluid ports as shown in FIG. 43.

Use of endoscopic portal 1110 is similar to that described above except that the universal seal 1116 is positioned to extend through an anatomical cavity wall W with the distal end 1118 thereof disposed in a body cavity and the proximal end 1120 thereof disposed externally of the body cavity. Positioning of the universal seal 1116 to extend through the cavity wall W can be accomplished with the use of a penetrating member disposed in the variable size passage 1147. During insertion through the cavity wall W by the penetrating member, the compressible member 1148 can be supplied with fluid to impart some rigidity to the compressible member, or the compressible member can be in a collapsed condition with no fluid supplied thereto since the elastic membrane 1170 will grip an instrument in the passage 1147. Insertion of the penetrating member through the universal seal 1116 is accomplished in the same manner as described below for the introduction of an instrument I through the universal seal 1116; however, the compressible member 1148 is normally not supplied with the compressible material when the penetrating member is inserted.

Figure 44:
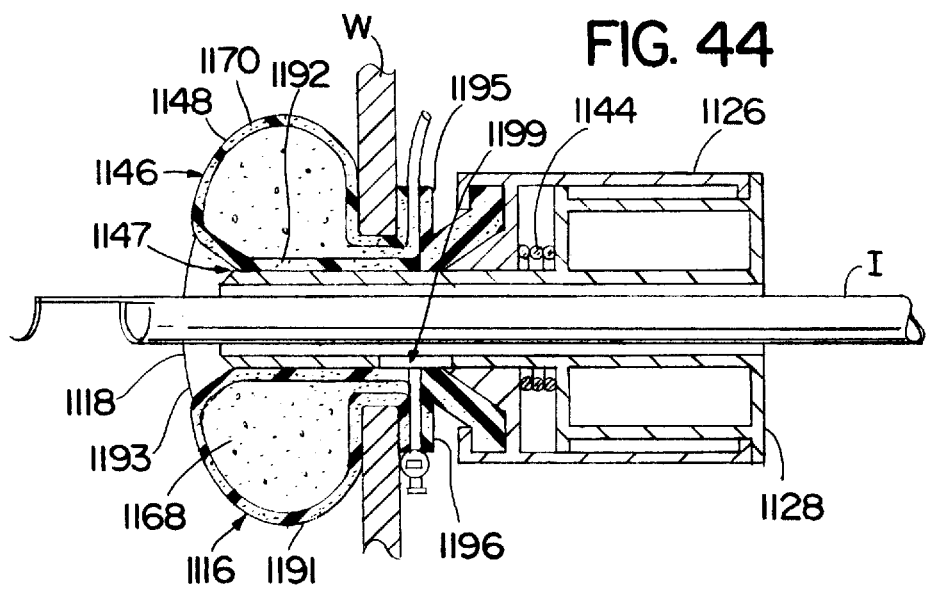
FIG. 44 is a broken sectional view of the endoscopic portal of FIG. 43 showing the universal seal in the open position.

Once the distal end 1118 of the seal 1116 has been positioned in the body cavity, compressible fluid 1168, such as gas or liquid, is supplied to the interior of membrane 1170 via port 1195 as shown by the arrows in FIG. 43. Accordingly, membrane 1170 will stretch causing the compressible member 1148 to expand. Expansion of the compressible member 1148 along the thickness of the cavity wall W will be limited due to the resistance presented by the cavity wall W; however, the compressible member will expand somewhat to sealingly engage the cavity wall W along the thickness thereof, i.e. along the opening in the cavity wall W through which the seal 1116 extends. The distal portion of the compressible member 1148 disposed within the body cavity will expand a greater amount to engage an internal surface of the cavity wall W. In this manner, the compressible member 1148 stabilizes the endoscopic portal as well as instruments introduced therethrough since the expanded seal member 1146 prevents the portal and instruments inserted therethrough from backing out of the body cavity. As shown in FIG. 43, the cavity wall W is held between the distal portion of the compressible member 1148 disposed in the body cavity and the ports 1195 and 1196 such that the portal is constrained against longitudinal movement. When it is desired to introduce an instrument into the body cavity, the housing 1114 is squeezed causing expander 1140 to be moved distally into variable size passage 1147. Movement of expander 1140 into variable size passage 1147 causes the seal 1116 to be moved from the closed position to an open position wherein the cross sectional size of the variable size passage 1147 is increased or enlarged and the expander 1140 provides a lumen through the seal member 1146 as shown in FIG. 44. An opening such as a slot 1199 or one or more perforations is provided in expander 1140 to be aligned with port 1196 when the seal 11 16 is in the open position such that insufflation gas can be supplied to the body cavity via port 1196 and the lumen of the expander 1140, and such fluid will be prevented from escaping once the universal seal 1116 has been returned to the normal closed position or placed in the sealing position. Instrument I is introduced at the body cavity through the lumen of expander 1140; and, once the instrument I extends through the universal seal 1116, the housing 1114 is released for return automatically to the non-compressed condition. Accordingly, expander 1140 will be withdrawn from the variable size passage, and compressible member 1148 will be in the sealing position with membrane inner wall 1192 sealingly contacting or engaging instrument I along the variable size passage 1147 to form a seal therewith and leakage of the insufflation gas being prevented.

Figure 45:
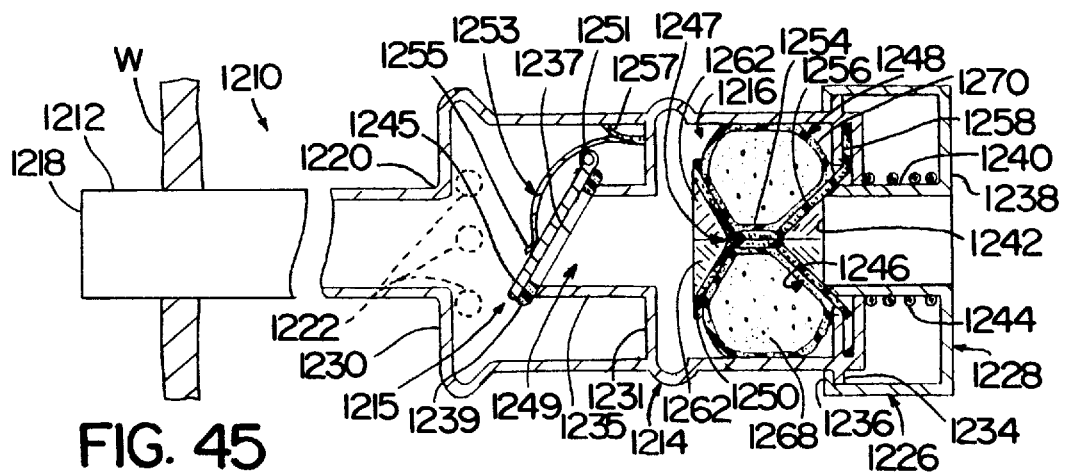
FIG. 45 is a broken, side sectional view of another modification of an endoscopic portal according to the present invention showing both the valve and the universal seal of the endoscopic portal in a closed position.

Another embodiment of an endoscopic portal according to the present invention is illustrated at 1210 in FIG. 45 and incorporates both a universal seal and a valve disposed distally of the seal. Endoscopic portal 1210 includes an elongate tubular member or sleeve 1212, a housing 1214 mounting a proximal end of tubular member 1212, a valve 1215 disposed in housing 1214, a universal seal 1216 disposed in housing 1214 proximally of valve 1215 and a tubular expander 1240 for opening seal 1216. Tubular member or sleeve 1212 has an open distal end 1218 for being disposed at an internal site in a body cavity, an open proximal end 1220 for being disposed externally of the body cavity and a lumen between the distal and proximal ends. The proximal end 1220 is coupled with housing 1214 and can be integrally, unitarily formed with a forward wall 1230 of housing 1214. It should be appreciated, however, that the tubular member can be made separate from the housing and can be coupled with or attached to the housing in many various ways either permanently or removably such as with the use of a threaded connection. Housing 1214 can be made of any suitable material, such as plastic, and can have various configurations including cylindrical and rectangular configurations. One or more ports 1222 are disposed on housing 1214 in communication with the interior thereof and in communication with the lumen of tubular member 1212. In the case of endoscopic portal 1210, the ports 1222 are provided at spaced locations along an enlarged or flared forward rim of housing 1214 as shown in dotted lines in FIG. 45. The ports 1222 can be designed in many various ways to be connectable with one or more supplies of fluid, such as insufflation gases or liquids, to be supplied to the body cavity. Housing 1214 includes main body 1226 and end cap 1228 slidably mounted on main body 1226. Main body 1226 includes transverse forward wall 1230, transverse intermediate wall 1231 and transverse end wall 1232 each having openings therein longitudinally aligned with the lumen of tubular member 1212. Main body 1226 has an enlarged intermediate rim to facilitate grasping. An inner tubular collar 1235 extends longitudinally, distally from intermediate wall 1231 with the lumen thereof aligned with the opening in intermediate wall 1231 and with the lumen of tubular member 1212. Collar 1235 terminates distally at an obliquely angled peripheral edge 1237 having a resilient ring, seal or band 1239 extending therealong defining a valve seat 1239.

Valve 1215 is in the nature of a conventional flapper valve typically used in endoscopic portals and includes a flapper or valve body 1245 pivotally mounted in housing 1214, a valve passage 1249 defined by the lumen of collar 1235 and the valve seat 1239 for being engaged by flapper 1245 to close the valve passage 1249. Flapper 1245 has a flat or planar section sufficiently large to engage the valve seat 1239 to cover the opening at the distal end of valve passage 1249 and an enlarged, cylindrical end section joined to the planar section. The cylindrical end section receives a shaft or pin 1251 extending transversely in housing 1214 between opposing side walls thereof, the shaft 1251 being perpendicular to a longitudinal axis of endoscopic portal 1210. Opposing ends of shaft 1251 are fixedly secured to the side walls of housing 1214 distally of intermediate wall 1231 to rotatably or pivotally mount flapper 1245. Flapper 1245 is rotatable or pivotable about shaft 1251 for movement from a closed position for valve 1215 wherein flapper 1245 is in sealing engagement with valve seat 1239 to close off or block communication between the valve passage 1249 and the tubular member lumen to an open position for valve 1215 wherein the flapper 1245 is pivoted or rotated out of engagement with the valve seat 1239 to open or establish communication between valve passage 1249 and the tubular member lumen. A spring 1253 disposed in housing 1214 biases flapper 1245 to the closed position, the spring 1253 having a curved or convex segment between an upwardly curved end 1255 in engagement with the valve body and an opposite, bent end 1257 in engagement with housing 1214. The spring 1253 can be secured to the flapper and/or the housing or the spring can be unsecured and held in place by the flapper and the housing. Spring 1253 resiliently biases the valve 1215 to the closed position while permitting the flapper 1245 to be pivoted or rotated about shaft 1251 to the open position against the bias of spring 1253. An operating member or lever can be connected to one end of shaft 1251 via a recess in the corresponding side wall of housing 1214 for manually moving the valve 1215 between the closed and open positions. It should be appreciated, however, that valve 1215 can be opened merely by manually inserting an instrument distally through the valve passage 1249 causing flapper 1245 to pivot away from the valve seat 1239. Representative flapper valves that can be utilized in the endoscopic portals include the valve disclosed in U.S. Pat. No. 4,654,030 to Moll et al and the valve utilized in the Endopath surgical trocar of Ethicon Endo-Surgery.

Universal seal 1216 is disposed in main body 1226 of housing 1214 between intermediate wall 1231 and end wall 1232. Universal seal 1216, which is the same as universal seal 16, includes seal member 1246 defining variable size passage 1247 and compressible member 1248 disposed around seal member 1246. Seal member 1246 is maintained in and/or biased to a closed, initial or contracted position by a spine (not shown) including a plurality of individual spring wires or stiffeners attached to seal member 1246 as explained for seal member 46. In the closed position, legs 1262 of seal member 1246 are biased inwardly toward one another, i.e. in the direction of the longitudinal axis of the seal member, such that inner surfaces or edges of the legs contact one another along intermediate section 1254. Accordingly, the variable size passage 1247 for seal 1216 is completely closed when the seal member 1246 is in the closed position prior to receiving an instrument; however, the variable size passage does not have to be completely closed in the initial position. Seal member 1246 is movable to an open, expanded or second position wherein legs 1262 are moved outwardly away from one another, i.e. in a direction transverse to the seal member longitudinal axis, to be spread apart from one another such that the variable size passage 1247 is open. Seal member 1246 is arranged in main body 1226 with rearward flange 1258 thereof fixedly received in a recess in end wall 1232 and with the variable size passage 1247 longitudinally aligned with or in communication with the valve passage 1249.

Compressible member 1248, which is similar to compressible member 48, includes a body of compressible material 1268 disposed around seal member 1246 and confined by housing 1214. Compressible member 1248 includes a bladder, bag, balloon or membrane 1270 made of any suitable expandable, stretchable, elastic, resilient or flexible material forming an envelope or bag for holding compressible material 1268 in the interior thereof. Membrane 1270 has a toroidal or donut-shape configuration with a central longitudinal passage entirely therethrough. The seal member 1246 is disposed in the passage of membrane 1270 with forward flange 1250 protruding from the membrane passage and with the slit ends disposed in the membrane passage to be covered by the compressible member 1248.

End cap 1228, which is integrally formed with expander 1240, is similar to end cap 28 and has an open forward or distal end with an inwardly protruding transverse flange 1236 and a transverse rearward or proximal wall 1238 having an opening therein aligned with variable size passage 1247. End cap 1228 is slidably mounted to the rearward end of main body 1226 with an outwardly protruding flange 1234 at the rearward end of main body 1226 being retained within the end cap 1228 by inwardly protruding flange 1236. Expander 1240 is tubular or hollow and extends distally from rearward wall 1238 with the lumen thereof aligned with the opening in the rearward wall 1238 and with the variable size passage 1247. A spring or bias member 1244 biases the end cap 1228 proximally from main body 1226 such that housing 1214 is normally disposed in a non-compressed condition, position or state with flange 1234 in abutment with flange 1236.

To use endoscopic portal 1210 to introduce instruments of various sizes in a body cavity, the distal end 1218 of tubular member 1212 is disposed at an internal site in a body cavity, and the proximal end 1220 of tubular member 1212 is disposed externally of the body cavity such that the lumen of tubular member 1212 provides a passage or portal establishing communication with the internal site from externally of the body cavity. Tubular member 1212 is typically positioned to extend through an anatomical wall W with the use of a penetrating member, such as a trocar, passing through the lumen of tubular member 1212 via the valve 1215 and the seal 1216. Passage of the penetrating member through seal 1216 and valve 1215 is accomplished in the same manner as described hereinafter for the introduction of various size instruments through the endoscopic portal. Seal member 1246 is in the normal closed position such that the variable size passage 1247 has a first cross-sectional size smaller than the cross-sectional size of the lumen of tubular member 1212. Housing 1214 is in the non-compressed condition with spring 1244 biasing end cap 1228 proximally from main body 1226. With the end cap 1228 biased from the main body 1226, the blunt distal end 1242 of expander 1240 is disposed slightly within the rearward section 1256 of seal member 1246 in contact with the sloping inner surfaces of legs 1262. Compressible member 1248 is disposed over the slits between the legs 1262 and exerts a closing force or positive pressure on seal member 1246. Valve 1215 disposed distally or upstream of seal 1216 is in the normal closed position with flapper 1245 biased by spring 1253 into engagement with valve seat 1239 to close off the valve passage 1249 such that fluid cannot flow through the endoscopic portal 1210. Once the distal end 1218 of tubular member 1212 has been positioned at the internal site, fluids, such as insufflation gas, can be introduced at the internal site via the ports 1222, and leakage of such fluids is prevented since the valve 1215 is closed.

Figure 46:
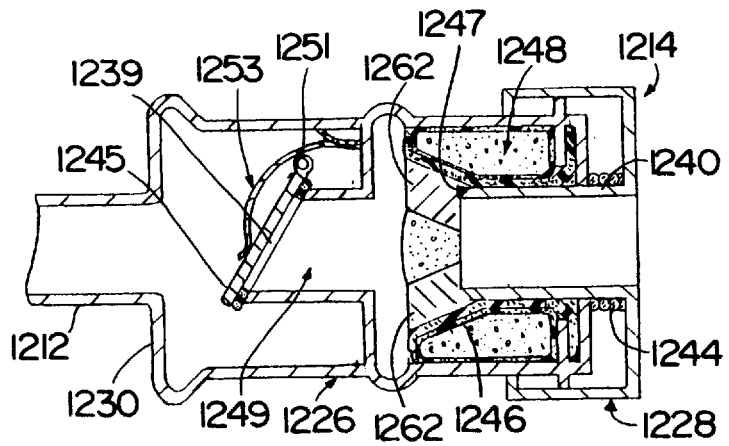
FIG. 46 is a broken, side sectional view of the endoscopic portal of FIG. 45 showing the valve in the closed position and the universal seal in the open position to receive an instrument.
Figure 48:
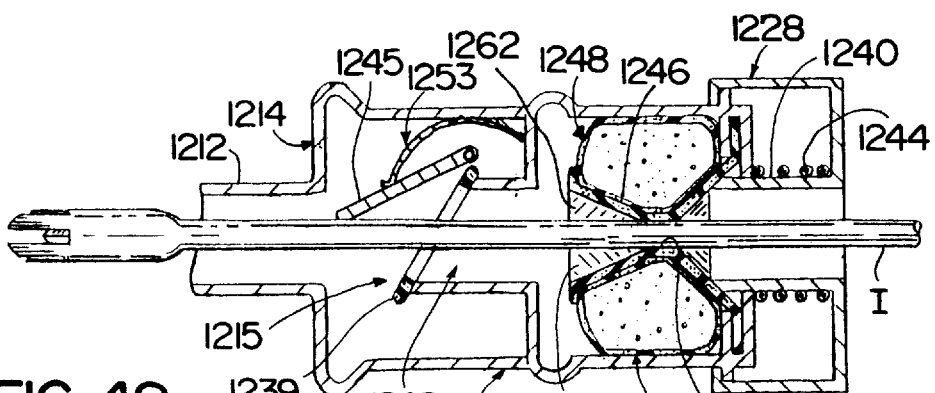
FIG. 48 is a broken, side sectional view of the endoscopic portal of FIG. 45 showing the valve in the open position to receive the instrument therethrough and the universal seal in the sealing position.

When it is desired to introduce an instrument at the internal site through the endoscopic portal 1210, housing 1214 is squeezed or compressed, moving end cap 1228 longitudinally, distally relative to the main body 1226 against the bias of spring 1244. Housing 1214 will then be in the compressed state, condition or position as shown in FIG. 46, and expander 1240 will be moved longitudinally, distally into the variable size passage 1247 to enlarge the variable size passage. Expander 1240 overcomes the closing force or bias of seal member 1246 and the compressive force of compressible member 1248 to spread legs 1262 apart from one another as facilitated by the angled, distal peripheral edge of the expander in contact with the inner surfaces of the legs of the seal member 1246. The legs 1262 are moved outwardly by expander 1240 in a direction transverse or radial to the longitudinal axis of endoscopic portal 1210 causing the seal member 1246 to be moved from the closed position to the open position wherein the variable size passage 1247 has a second cross-sectional size larger than the first cross-sectional size. Once the distal end of expander 1240 has passed through intermediate section 1254, the seal member 1246 will be in a fully open position with legs 1262 biased into engagement or contact with the outer surface of expander 1240. Movement of the seal member 1246 to the open position compresses compressible member 1248 which exerts an increased compressive force against the seal member since the compressible member is confined by the seal member 1246 and the housing 1214. Therefore, the seal 1216 forms a seal with the expander 1240 due to the closing force or bias of the seal member 1246 and the compressive force of the compressible member 1248, which fills the gaps or spaces between the legs 1262 and sealingly contacts the expander between the legs to form a seal entirely around the periphery or circumference of the expander. With the seal 1216 in the open position forming a seal with expander 1240, the valve 1215 remains closed with flapper 1245 preventing fluid flow across the valve such that leakage or desufflation through the endoscopic portal is prevented even though the variable size passage 1247 has been enlarged or opened as shown in FIG. 46. The lumen of expander 1240 provides a passage through the seal member 1246 such that instruments having various cross-sectional sizes larger than the first cross-sectional size can passage without coming into contact with the seal 1216. With the seal 1216 maintained in the open position by the expander 1240, an instrument I having a cross-sectional size larger than the first cross-sectional size and the same as or smaller than the cross-sectional size of the lumen of the expander 1240 is inserted through the lumen of the expander such that the instrument I extends through the seal 1216. End cap 1228 is released allowing the housing 1214 to automatically return to the non-compressed state with expander 1240 withdrawn from the variable size passage 1247. Once the housing 1214 has returned to the non-compressed state, the universal seal 1216 will be in the sealing position with seal member 1246 urged toward the closed position due to the bias thereof as well as due to the force of compressible member 1248. Accordingly, universal seal 1216 engages the instrument I to form a seal therewith in the same manner as the seal formed with expander 1240 in that legs 1262 are biased into sealing engagement with instrument I and compressible member 1248 fills the spaces between legs 1262 to sealingly contact instrument I to form a seal entirely around the periphery or circumference of instrument I while allowing the instrument I to be moved longitudinally through the variable size passage 1247 as shown in FIG. 47. Once the universal seal 1216 is in the sealing position forming a seal with instrument I, the valve 1215 is moved from the normally closed position to the open position via the operating member or via distal movement of instrument I against flapper 1245 as shown in FIG. 47. Accordingly, valve 1215 is not opened until after the universal seal 1216 is in the sealing position such that leakage through the endoscopic portal 1210 is prevented when valve 1215 is opened. The instrument I is moved distally through the valve passage 1249 into the lumen of tubular member 1212 to position a distal end of the instrument in the body cavity, and the valve 1215 is held in an open position due to the presence of instrument I in the valve passage 1249 as shown in FIG. 48. When instrument I is withdrawn from the endoscopic portal 1210, the instrument is first withdrawn from the valve passage 1249, such that the valve 1215 automatically returns to the closed position before the instrument is withdrawn from the seal 1216. The instrument is slidably withdrawn from the seal 1216 after the valve is in the closed position, and the seal thereafter automatically returns to the closed position.

A further modification of an endoscopic portal according to the present invention is illustrated in FIG. 49 at 1310. Endoscopic portal 1310 is similar to endoscopic portal 1210 except that endoscopic portal 1310 includes a trumpet or slide valve and is illustrative of a design wherein either or both of the valve and the universal seal are add-on components. Endoscopic portal 1310 includes tubular member 1312, valve housing 1314A mounting a proximal end of tubular member 1312, valve 1315 disposed in valve housing 1314A, universal seal 1316 disposed proximally of valve 1315, seal housing 1314B mounting universal seal 1316 and expander 1340 for enlarging the variable size passage 1347 of seal 1316. Valve housing 1314A has a forward wall 1330 with a threaded opening therethrough receiving an externally threaded proximal end 1320 of tubular member 1312 such that the valve housing 1314A is removably attached to the tubular member. Valve housing 1314A has an end wall 1331 with an opening therethrough longitudinally aligned with the opening in the forward wall 1330 and with the lumen of tubular member 1312. A cylindrical cavity 1361 is formed in the valve housing 1314A transverse or perpendicular to a longitudinal axis of endoscopic portal 1310 and in communication with the openings through the forward and end walls. Valve 1315 is in the nature of a trumpet or slide valve used in endoscopic portals and includes a valve body 1345, a bias member 1353 for biasing the valve body 1345 to be disposed in a closed position and a stop 1363 for limiting movement of the valve body 1345 to an open position. The valve body 1345 has a cylindrical section or portion 1367 disposed in the cylindrical cavity 1361, a cylindrical shaft 1369 extending from cylindrical portion 1367 through an opening in a side wall of housing 1314A and a cylindrical protrusion 1388 protruding from cylindrical portion 1367 opposite shaft 1369. A diametrical bore is formed in the cylindrical portion 1367 and defines a valve passage 1349. The valve body 1345 may be provided with guide posts that fit within slots formed in the housing 1314A to prevent rotation of the valve body 1345 while permitting the valve body to move longitudinally in the cylindrical cavity 1361. The stop 1363, which cooperates with protrusion 1388 to limit axial or longitudinal movement of the valve body, has a cylindrical body axially aligned with the protrusion 1388 and a pair of circumferential collars 1302 axially spaced from one another along the cylindrical body. The cylindrical body of the stop 1363 extends through a side wall of the housing 1314A with the side wall received between the circumferential collars 1302. The bias member 1353 is in the nature of a coiled spring 1353 disposed in cavity 1361 between the stop 1363 and the valve body 1345, the spring 1353 being disposed around the cylindrical protrusion 1388 of the valve body and around the cylindrical body of the stop 1363. The spring 1353 biases the valve body 1345 axially or longitudinally away from the stop 1363 such that the valve is disposed in a normal closed position wherein the valve passage 1349 is not aligned with the openings in the forward and end walls. Accordingly, the solid section of cylindrical portion 1367 of the valve body 1345 is disposed in longitudinal alignment with the openings in the forward and end walls to completely close off or block the lumen of tubular member 1312 such that fluid flow through the valve housing 1314A is prevented when the valve 1315 is in the closed position. The valve 1315 is movable to an open position by manually moving the valve body 1345 longitudinally or axially toward the stop 1363 via the protruding shaft 1369 until the cylindrical protrusion 1388 engages the cylindrical body of the stop 1363. Accordingly, the valve passage 1349 of the valve body 1345 will then be in alignment with the openings in the forward and end walls and, therefore, with the lumen of tubular member 1312, such that a passage is defined through the valve housing 1314A into the tubular member lumen. U.S. Pat. No. 4,601,710 to Moll and No. 3,817,251 to Hasson are illustrative of trumpet or slide valves that can be utilized in the endoscopic portals.

Universal seal 1316 is similar to universal seal 1216 except that universal seal 1316 is disposed in a separate seal housing 1314B having pivotable detents 1303 at a forward end thereof for removably attaching or coupling the seal housing 1304B with the valve housing 1314A. Seal housing 1314B includes main body 1326 and end cap 1328 slidably mounted to main body 1326. The detents 1303 are secured to the seal housing 1314B adjacent a forward wall 1304 of main body 1326 and include locking fingers having ends pivotally secured to housing 1314B with the fingers extending distally to terminate at bent or angled ends defining catches for being engaged in recesses in the end wall 1331 of valve housing 1314A. The detents are flexible, bendable, pivotable or resilient allowing the fingers to bend, flex, pivot or bend outwardly about the ends secured to seal housing 1314B as shown by the arrows in FIG. 49 to disengage the catches from valve housing 1314A to detach the valve housing 1314A from the seal housing 1314B. The forward wall 1304 of the seal housing 1314B has an opening therein aligned with the opening in the end wall 1331 of the valve housing 1314A, and the opening in the forward wall 1304 is threaded to threadedly connect tubular member 1312 or another selected tubular member to the seal housing 1314B where the seal housing 1314B is detached from valve housing 1314A for use without a valve. Accordingly, the seal housing 1314B is detachable from the valve housing 1314A allowing use of the seal 1316 without a valve or with another selected valve and allowing use of valve 1315 without a seal or with another selected universal seal. Main body 1326 includes end wall 1332 mounting rearward flange 1358 of seal member 1346 and end cap 1328 is mounted on a rearward end of main body 1326. End cap 1328 is biased proximally from main body 1326 by spring 1344 such that seal housing 1314B is disposed in a non-compressed condition with the distal end of expander 1340 disposed slightly in the rearward section 1356 of seal member 1346.

Figure 50:
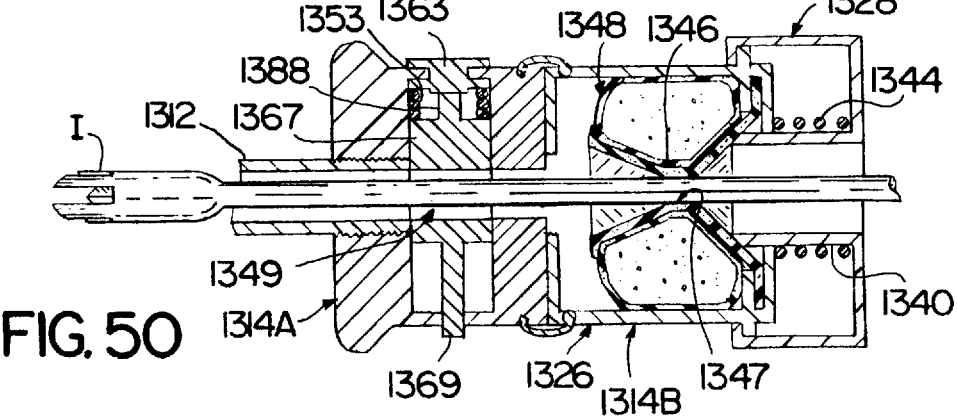
FIG. 50 is a broken, side sectional view of the endoscopic portal of FIG. 49 showing the universal seal in the sealing position and the valve in the open position.

Use of endoscopic portal 1310 is similar to that described above except that detents 1303 are used to couple the seal housing 1314B with the valve housing 1314A prior to receiving an instrument. When it is desired to introduce an instrument in the lumen of tubular member 1312, the seal housing 1314B is compressed or squeezed causing the expander 1340 to be moved distally into the seal member 1346 to move the seal member 1346 from the normal closed position to the open position to enlarge variable size passage 1347 while the valve 1315 remains in its normal closed position. An instrument I is inserted through the lumen of the expander 1340 and the seal housing 1314B is released for return to the non-compressed state. The seal member 1346 and the compressible member 1348 thereafter form a seal with the instrument I in the variable size passage 1347 as shown in FIG. 50. Once the universal seal 1316 forms a seal with the instrument I, the valve 1315 is moved from the closed position to the open position by depressing the shaft 1369 to move the valve body 1345 inwardly toward the stop 1363 to axially or longitudinally align the valve passage 1349 with the openings in the forward and end walls of valve housing 131 4A and with the lumen of tubular member 1312 as shown in FIG. 50. The instrument I is then moved distally through the valve passage 1349 into the lumen of the tubular member 1312. Since the universal seal 1316 is in a sealing position with the instrument I, fluid flow through the endoscopic portal 1310 is prevented when the valve 1315 is open.

With the endoscopic portals according to the present invention, a universal seal is opened with the use of a blunt expander allowing instruments to be inserted through the seal via the expander without contacting the universal seal. Accordingly, the universal seals can be made of resilient, elastic materials while avoiding the risk of tearing or puncturing the elastic materials of the seal when instruments are passed therethrough. The universal seals can be designed with or without a compressible member and include a seal member normally disposed in a closed position wherein a variable size passage of the seal member has a first cross sectional size. Where the variable size passage is completely closed in the closed position, the universal seal can serve as a valve in place of conventional trocar or portal valves. The endoscopic portals can include various valves, such as conventional flapper, ball and trumpet valves, as well as the distal end valve disclosed in applicant's prior application Ser. No. 08/383,520 filed Feb. 3, 1995 and incorporated herein by reference, for preventing fluid flow through the endoscopic portals when the seals are opened. The upstream valves are not opened until after the seals are in the sealing position such that fluid flow through the endoscopic portals is prevented when the valves are opened. Where the endoscopic portals include both a valve and a universal seal, both the valve and seal can be arranged in the housing. Alternatively, the valve can be disposed in the housing and the seal can be an add-on component attachable to the housing. The seal members can be normally disposed in the closed position due to the configuration and/or materials of the seal members or with the use of a spine or stiffener. The seal members can have slits defining resilient legs or pivotal or bendable members, or the seal members can be essentially continuous solid structures. Where the seal members are provided with spreadable legs, the universal seals can include a compressible member disposed around the seal members or a stretchable inner layer along an inner surface of the seal members to sealingly contact an instrument along the spaces between the legs. The seal members can comprise multiple layers or seal members; and, where the multiple seal members are each slit, the slits of the seal members can be non-aligned such that the slits of the inner seal member are covered by solid portions of the outer seal member with the slits of the outer seal member being disposed over solid portions of the inner seal member. The seal members can include various bias devices such as a spine disposed on or within the material of the seal members or a stretchable ring disposed around the seal members, and the compressible members can function as a bias device to bias the seal members to the closed position. The seal members can have various configurations including various configurations providing gradual opening of the variable size passages by the distal end of the expander. It should be appreciated that the seal members can be biased toward the open position and maintained in the closed position by the expanders and/or the compressible members. The endoscopic portals according to the present invention can be designed with the seal member attached to the end cap and movable to the open position in response to movement of the seal member into the main body of the housing via squeezing operation of the housing. Depending upon the configuration of the seal member, a seal can be formed with an introduced instrument along the entire or most of the entire length of the seal member or the entire or most of the entire length of the variable size passage, or at discrete locations along the length of the seal member or the variable size passage. The compressible members can serve as the seal members for the endoscopic portals. The universal seals can extend through a cavity wall to provide a passage communicating with the cavity and for receiving instruments such that the seals serve as a portal sleeve. The expanders can have various distal end configurations to cooperate with the configurations of the seal members to facilitate opening of the variable size passages. The expanders can be utilized with any elastic universal seal, in addition to those shown herein, to open such seal to receive an instrument. With the universal seals of the present invention, instruments inserted therethrough are movable longitudinally through the seal members while a seal is maintained with the instruments. The universal seals can be provided in the main body of the housing, in the end cap or partly within the main body and partly within the end cap. Depending on the size of instruments to be inserted in the seal members, the instruments can be inserted with the seal members partially open or with the seal members fully open. The compressible members can be designed in many various ways to apply a compressive or sealing force against the seal members to form a seal with an inserted instrument. Where the compressible members include a body of compressible material disposed around the seal members, the compressible members can occupy or fill any gaps or spaces created when the seal members are moved to the open position and to contact the inserted instruments to complete the seal therewith. The endoscopic portals according to the present invention can be partially or entirely reusable or disposable for single patient use.

In as much as the present invention is subject to many modifications, variations and changes in detail, it is intended that all subject matter discussed above or shown in the drawings be interpreted as illustrative only and not to be taken in a limiting sense.

What is claimed is:

1. An endoscopic portal for establishing communication with a body cavity for the introduction of instruments through the endoscopic portal comprising a resilient seal member having a variable size passage for communication with the body cavity to permit instruments of various cross sectional sizes to extend through said variable size passage for introduction of distal ends of the instruments in the body cavity, said seal member being disposed in a closed position wherein said variable size passage is closed and being movable to an open position wherein said variable size passage is open;

a tubular expander aligned with said variable size passage and being insertable in said seal member to move said seal member from said closed position to said open position such that instruments of various cross sectional sizes can be introduced through said tubular expander and said seal member to extend through said variable size passage, said tubular expander being withdrawable from said seal member such that instruments of various cross sectional sizes introduced through said tubular expander and said seal member remain in said variable size passage to extend therethrough a mass of compressible material disposed externally around said seal member with said variable size passage extending longitudinally within said mass of compressible material and a housing confining said mass of compressible material therein such that said mass of compressible material is compressed within said housing when said tubular expander is inserted in said seal member and when instruments of various cross sectional sizes extend through said variable size passage after said tubular expander is withdrawn from said seal member, said mass of compressible material exerting a compressive force on said seal member such that said seal member sealingly engages instruments of various cross sectional sizes in said variable size passage to form a seal therewith.

2. An endoscopic portal as recited in claim 1 wherein said seal member includes a stretchable membrane having a longitudinally elongate opening therethrough defining said variable size passage, said tubular expander being insertable in said opening to stretch said membrane to enlarge said opening to receive said tubular expander in sealing relation therewith.

3. An endoscopic portal as recited in claim 1 wherein said compressible material is a compressible solid substantially filling said housing.

4. An endoscopic portal as recited in claim 1 wherein said compressible material is a compressible fluid substantially filling said housing.

5. An endoscopic portal as recited in claim 1 wherein said mass of compressible material is enclosed in a stretchable membrane disposed within said housing.

6. An endoscopic portal for establishing communication with a body cavity for the introduction of instruments through the endoscopic portal comprising a cannula having a distal end for being disposed in a body cavity, a proximal end for being disposed externally of the body cavity and a lumen between said distal and proximal ends having a cross sectional size;

a seal member defining a variable size passage communicating with said lumen, said seal member being biased to a contracted position wherein said variable size passage has a first cross sectional size smaller than the cross sectional size of said lumen and being movable to an expanded position wherein said variable size passage has a second cross sectional size larger than said first cross sectional size;

a tubular expander having a lumen aligned with said variable size passage, said lumen having a cross sectional size larger than said first cross sectional size, said tubular expander being movable into said variable size passage to move said seal member from said contracted position to said expanded position such that an instrument having a cross sectional size larger than said first cross sectional size can be inserted through said seal member and said variable size passage, said tubular expander being withdrawable from said variable size passage such that the inserted instrument remains in said variable size passage to extend therethrough;

a spine carried by said seal member and providing an internal bias force biasing said seal member toward said contracted position; and a compressible member disposed externally of said seal member and providing an external bias force biasing said seal member toward said contracted position, said internal and external bias forces biasing said seal member into engagement with the inserted instrument to form a seal therewith.

7. An endoscopic portal as recited in claim 6 and further including a housing at said proximal end of said cannula and wherein said seal member and said compressible member are disposed in said housing.

8. An endoscopic portal as recited in claim 7 wherein said compressible member is encapsulated in a membrane.

9. An endoscopic portal for establishing communication with a body cavity for the introduction of instruments through the endoscopic portal comprising a cannula having a distal end for being disposed in a body cavity, a proximal end for being disposed externally of the body cavity and a lumen between said distal and proximal ends having a cross sectional size;

a housing at said proximal end of said cannula;

a seal including a seal member disposed in said housing and defining a variable size passage communicating with said lumen, said seal member being biased to a contracted position wherein said variable size passage has a first cross sectional size smaller than the cross sectional size of said lumen and being movable to an expanded position wherein said variable size passage has a second cross sectional size larger than said first cross sectional size, said seal including a compressible member disposed in said housing and exerting a compressive sealing force on said seal member when said seal is in said expanded position, said compressible member including a bladder filled with a compressible material disposed around said seal member and confined by said housing; and a tubular expander having a lumen aligned with said variable size passage, said lumen having a cross sectional size larger than said first cross sectional size, said tubular expander being movable into said variable size passage to move said seal from said contracted position to said expanded position such that an instrument having a cross sectional size larger than said first cross sectional size can be inserted through said seal into said lumen of said tubular member, said tubular expander being withdrawable from said variable size passage such that said seal is biased into engagement with the inserted instrument to form a seal therewith.

10. An endoscopic portal as recited in claim 9 wherein said compressible material includes a compressible sponge.

11. An endoscopic portal as recited in claim 9 wherein said compressible material includes a compressible fluid.

12. An endoscopic portal as recited in claim 11 wherein said compressible material includes a gas.

13. An endoscopic portal as recited in claim 1 wherein said seal member is internally biased to said closed position.

14. An endoscopic portal as recited in claim 13 wherein said seal member is made of shape memory material internally biasing said seal member to said closed position.

15. An endoscopic portal as recited in claim 13 and further including a spine carried by said seal member and internally biasing said seal member to said closed position.

16. An endoscopic portal as recited in claim 1 wherein said seal member includes a plurality of resilient legs disposed around said variable size passage, said legs being biased inwardly toward one another in said closed position to close said variable size passage, said legs being movable outwardly away from one another to open said variable size passage in said open position, said legs being spaced from one another in said open position to define spaces therebetween expanded position and further including a body of compressible material disposed around, said mass of compressible material entering and filling said spaces to sealingly engage instruments of various cross sectional sizes in said variable size passage.

17. An endoscopic portal as recited in claim 1 wherein said seal member includes a plurality of block members arranged around a longitudinal axis of said variable size passage and urged inwardly toward one another by said compressible member.

18. An endoscopic portal as recited in claim 2 wherein said membrane has a hollow conical configuration tapering to a distal end and said opening is disposed at said distal end of said membrane.

19. An endoscopic portal as recited in claim 1 wherein said variable size passage is completely closed in said closed position.

20. An endoscopic portal for establishing communication with an internal site in a body for the introduction of instruments through the endoscopic portal comprising
 a cannula having a distal end for being disposed at an internal site in a body, a proximal end for being disposed externally of the body, a longitudinal axis, a lumen between said distal and proximal ends for receiving instruments of various sizes and a housing at said proximal end having an external wall;
 a seal member disposed in said housing and having a variable size passage aligned with said lumen, said seal member being resiliently biased toward said longitudinal axis in a contracted position to contract said variable size passage;
 a body compressible material disposed externally around said seal member and substantially filling said housing, said body of compressible material being confined in said housing in contact with said seal member and said external wall of said housing; and
 a tubular expander coupled with said seal member in alignment with said variable size passage and having a blunt end, said blunt end being movable into said variable size passage to enlarge said variable size passage such that an instrument can be inserted through said seal member and said tubular expander without contacting said seal member, said body of compressible material being compressed between said seal member and said external wall of said housing to exert a compressive sealing force on said tubular expander when said tubular expander is moved into said variable size passage, said blunt end being withdrawable from said variable size passage leaving the instrument to extend through said seal member such that said body of compressible material is compressed between said seal member and said external wall of said housing to exert a compressive sealing force on said seal member biasing said seal member into engagement with the instrument to form a seal therewith.

21. An endoscopic portal as recited in claim 20 wherein said seal member is made of rubber.

22. An endoscopic portal as recited in claim 21 wherein said seal member includes an elastic membrane having an opening therethrough defining said variable size passage.

23. An endoscopic portal as recited in claim 22 wherein said blunt end of said expander is rounded.

24. An endoscopic portal as recited in claim 20 wherein said seal member has an internal configuration cooperating with the configuration of said blunt end to incrementally enlarge said variable size passage as said blunt end is moved into said variable size passage.

25. A method of introducing an instrument in a body cavity comprising the steps of
 providing a sleeve having a distal end, a proximal end and a lumen between the distal and proximal ends, a housing at the proximal end, a resilient seal member disposed in the housing and having a variable size passage communicating with the lumen, the seal member being biased to a contracted position to close the variable size passage, a tubular expander longitudinally aligned with the variable size passage and having a blunt end and a mass of compressible material disposed around the seal member and substantially filling the housing with the mass of compressible material confined by the housing;
 introducing the distal end of the sleeve in a body cavity;
 moving the blunt end of the tubular expander into the variable size passage to open the variable size passage to receive an instrument;
 compressing the mass of compressible material within the housing in response to opening of the variable size passage by the tubular expander such that the mass of compressible material biases the seal member into sealing engagement with the tubular expander;
 introducing an instrument in the body cavity through the tubular expander with the tubular expander disposed in the variable size passage such that the instrument extends through the seal member into the lumen;
 withdrawing the tubular expander from the variable size passage such that the instrument remains in the variable size passage and extends therethrough;
 moving the seal member toward the contracted position to engage the instrument in response to withdrawal of the tubular expander from the variable size passage; and
 compressing the mass of compressible material within the housing in response to presence of the instrument in the variable size passage such that the mass of compressible material biases the seal member into sealing engagement with the instrument.

26. A method of introducing an instrument in a body cavity as recited in claim 25 wherein the housing has a non-compressed position wherein the blunt end of the tubular expander is withdrawn from the variable size passage and a compressed position wherein the blunt end of the tubular expander is within the variable size passage, and said step of moving the blunt end of the tubular expander into the variable size passage includes compressing the housing for movement from the non-compressed position to the compressed position.

27. A method of introducing an instrument in a body cavity as recited in claim 26 wherein the housing is biased to the non-compressed position and said step of withdrawing includes releasing the housing for movement from the compressed position to the non-compressed position.

28. A method of introducing an instrument in a body cavity as recited in claim 25 and further including, subsequent to said step of compressing the mass of compressible material in response to presence of the instrument in the variable size passage, the steps of repeating the step of moving the blunt end of the tubular expander into the variable size passage, withdrawing the instrument through the tubular expander to withdraw the instrument from the body cavity and the seal member and repeating the step of withdrawing the blunt end of the tubular expander from the variable size passage to move the seal member to the contracted position to close the variable size passage.

* * * * *